(12) United States Patent
Wong et al.

(10) Patent No.: US 12,280,141 B2
(45) Date of Patent: Apr. 22, 2025

(54) LIQUID DEPOT FOR NON-INVASIVE SUSTAINED DELIVERY OF AGENTS TO THE EYE

(71) Applicant: CHIBI, INC., Menlo Park, CA (US)

(72) Inventors: Vernon G. Wong, Menlo Park, CA (US); Glenn T. Huang, Fremont, CA (US)

(73) Assignee: Chibi, Inc., Menlo Park, CA (US)

( * ) Notice: Subject to any disclaimer, the term of this patent is extended or adjusted under 35 U.S.C. 154(b) by 0 days.

(21) Appl. No.: 17/547,028

(22) Filed: Dec. 9, 2021

(65) Prior Publication Data

US 2022/0168219 A1 Jun. 2, 2022

Related U.S. Application Data

(63) Continuation of application No. 16/909,242, filed on Jun. 23, 2020, now Pat. No. 11,234,926, which is a continuation of application No. PCT/US2019/030294, filed on May 1, 2019.

(60) Provisional application No. 62/665,367, filed on May 1, 2018.

(51) Int. Cl.
| | |
|---|---|
| A61K 31/5575 | (2006.01) |
| A61K 9/00 | (2006.01) |
| A61K 31/355 | (2006.01) |
| A61K 31/4709 | (2006.01) |
| A61K 31/573 | (2006.01) |
| A61K 31/575 | (2006.01) |
| A61K 47/14 | (2017.01) |
| A61K 47/22 | (2006.01) |
| A61P 27/02 | (2006.01) |
| A61P 27/06 | (2006.01) |

(52) U.S. Cl.
CPC ........ *A61K 9/0048* (2013.01); *A61K 31/4709* (2013.01); *A61K 31/573* (2013.01); *A61K 31/575* (2013.01); *A61K 47/14* (2013.01); *A61K 47/22* (2013.01)

(58) Field of Classification Search
None
See application file for complete search history.

(56) References Cited

U.S. PATENT DOCUMENTS

| | | |
|---|---|---|
| 5,869,079 A | 2/1999 | Wong et al. |
| 6,331,313 B1 | 12/2001 | Wong et al. |
| 7,906,136 B2 | 3/2011 | Wong et al. |
| 8,470,873 B2 | 6/2013 | Chen |
| 8,541,413 B2 | 9/2013 | Wong et al. |
| 8,722,728 B2 | 5/2014 | Wong et al. |
| 8,957,110 B2 | 2/2015 | Aleo et al. |
| 9,011,915 B2 | 4/2015 | Wong et al. |
| 9,144,566 B2 | 9/2015 | Wong et al. |
| 9,289,428 B2 | 3/2016 | Wong et al. |
| 9,474,736 B2 | 10/2016 | Wong et al. |
| 9,585,959 B2 | 3/2017 | Tiberg et al. |
| 9,737,606 B2 | 8/2017 | Wong et al. |
| 9,814,773 B2 | 11/2017 | Wong et al. |
| 9,993,558 B2 | 6/2018 | Wong et al. |
| 10,744,202 B2 | 8/2020 | Wong et al. |
| 11,234,926 B2 | 2/2022 | Wong et al. |
| 11,497,710 B2 | 11/2022 | Wong et al. |
| 2006/0073182 A1 | 4/2006 | Wong et al. |
| 2008/0085263 A1 | 4/2008 | Thuresson et al. |
| 2008/0260832 A1 | 10/2008 | Burke et al. |
| 2009/0082337 A1 | 3/2009 | Venkastesh et al. |
| 2013/0017244 A1 | 1/2013 | Huang et al. |
| 2013/0046014 A1* | 2/2013 | Theisinger ........... A61K 9/0048 514/622 |
| 2013/0324481 A1* | 12/2013 | Wong ..................... A61K 47/22 514/259.41 |
| 2014/0329785 A1 | 1/2014 | Chandran et al. |
| 2015/0343071 A1 | 12/2015 | Vangara et al. |
| 2018/0000729 A1 | 1/2018 | Tamraz et al. |
| 2020/0368153 A1 | 11/2020 | Wong et al. |
| 2024/0285520 A1 | 8/2024 | Wong et al. |

FOREIGN PATENT DOCUMENTS

| | | | |
|---|---|---|---|
| EP | 3272362 A1 | 1/2018 | |
| WO | WO 01/22937 | 4/2001 | |
| WO | WO-0197774 A2 * | 12/2001 | ............. A61K 38/13 |
| WO | WO-2013090842 A2 * | 6/2013 | ........... A61K 31/407 |

OTHER PUBLICATIONS

Kent, What Is the Difference Between D-Alpha & Dl-Alpha Tocopheryl Acetate?, www.Livestrong.com, Jul. 5, 2014, printed from https://web.archive.org/web/20140705132006/https://www.livestrong.com/article/545591-what-is-the-difference-between-d-alpha-dl-alpha-tocopheryl-acetate/, 3 pages.*
Rowe et al., Medium-chain triglycerides, Handbook of Pharmaceutical Excipients, 2009, Sixth Edition, Pharmacuetical Press, 429-431.*
Alayoubi et al., "Vitamin E" fortified parenteral lipid emulsions: Plackett-Burman screening of primary process and composition parameters. Drug Dev Ind Pharm. Feb. 2013;39(2):363-73. doi: 10.3109/03639045.2012.682223. Epub May 4, 2012.*
U.S. Appl. No. 16/909,591, Non-Final Office Action, mailed on Aug. 17, 2021, 12 pages.
European Application No. 19796932.2, Extended European Search Report, mailed on Dec. 7, 2021, 7 pages.
International Application No. PCT/US2019/030294, International Preliminary Report on Patentability, mailed on Nov. 12, 2020, 8 pages.
International Application No. PCT/US2019/030294, International Search Report and Written Opinion, mailed on Jul. 9, 2019, 3 pgs (ISR) and 6 pgs (written opinion).

(Continued)

*Primary Examiner* — Gigi G Huang
(74) *Attorney, Agent, or Firm* — Sheridan Ross P.C.

(57) ABSTRACT

The present embodiments provide compositions, methods, and kits for the treatment or prevention of ocular conditions or maladies via non-invasive liquid depots. In at least one embodiment, the liquid depot is capable of sustained-release delivery of at least one pharmaceutical agent to the eye for days or weeks.

7 Claims, 9 Drawing Sheets

(56) References Cited

OTHER PUBLICATIONS

China National Intellectual Property Administration; First Office Action; CN Application No. 201980044591.3; mailed Feb. 25, 2023; 15 pgs (with translation).
PubChem, Compound Summary, Decanoy/octanoyl-glycerides, date: Feb. 16, 2015, 11 pages.
Duker "Sustained-release drug delivery products edge closer to fruition," Healio, May 3, 2016, 8 pages.

* cited by examiner

LIQUID DEPOT FOR NON-INVASIVE SUSTAINED DELIVERY OF AGENTS TO THE EYE

RELATED APPLICATION

The present application is a continuation of U.S. application Ser. No. 16/909,242, filed Jun. 23, 2020, now U.S. Pat. No. 11,234,926, which application is a continuation of International Application No. PCT/US2019/030294, filed May 1, 2019, which claims priority benefit of U.S. Provisional Application No. 62/665,367, filed May 1, 2018, the disclosures of which are hereby incorporated by reference in their entirety for all purposes.

The present embodiments provide compositions and methods for the treatment of ocular conditions or maladies.

BACKGROUND

There remains a need for noninvasive, sustained delivery of pharmaceutical agents to tissues and liquid portions of the eye, such as the conjunctiva, cornea, or aqueous humor.

SUMMARY

The present embodiments provide compositions and methods for treating or preventing ocular ailments via a non-invasive liquid depot capable of delivering at least one pharmaceutical agent to the eye for days or weeks. This liquid depot is biocompatible and adapts to the shape of the eye, forming a thin film or flat bubble that covers the exterior tissues of the eye (e.g., conjunctiva, corneal surface) and is resistant to lacrimation (e.g., tears); although this film remains in place for days or over a week, it does not impair vision after initial instillation; and instillation is mediated, at least in part, by viscosity of the liquid depot; this depot formulation can be used to deliver pharmaceutical agent(s) to various parts of the eye where it can be detected for over the course of days or in some circumstances, over three weeks after a single administration. Remarkably, although this liquid depot remains on the outside of the eye, pharmaceutical agent(s) can be delivered into ocular tissues (e.g., cornea) and fluids (e.g., the aqueous humor) inside the eye for at least an entire day, at least three (3) days, and in some embodiments, at least seven (7) days. As such, effective intermittent administration (e.g., once a day, once every 3 days, or longer) of a single-dose liquid depot comprising at least one pharmaceutical agent is made possible with the present embodiments, in marked contrast to the multiple daily doses required with current commercial ocular formulations.

The liquid depot described herein provides sustained release of pharmaceutical agent(s) at a steadier release rate (i.e., decreased "spike"), fewer side effects, and/or with superior efficacy compared with current aqueous-based eye drops. In some embodiments, the continuous levels of pharmaceutical agent released from the liquid depot provides efficacious benefit at $C_{max}$ concentrations of pharmaceutical agent below those previously thought to be required to achieve clinical benefit, based on comparison with current aqueous-based eye drops.

DETAILED DESCRIPTION

Figure 1:
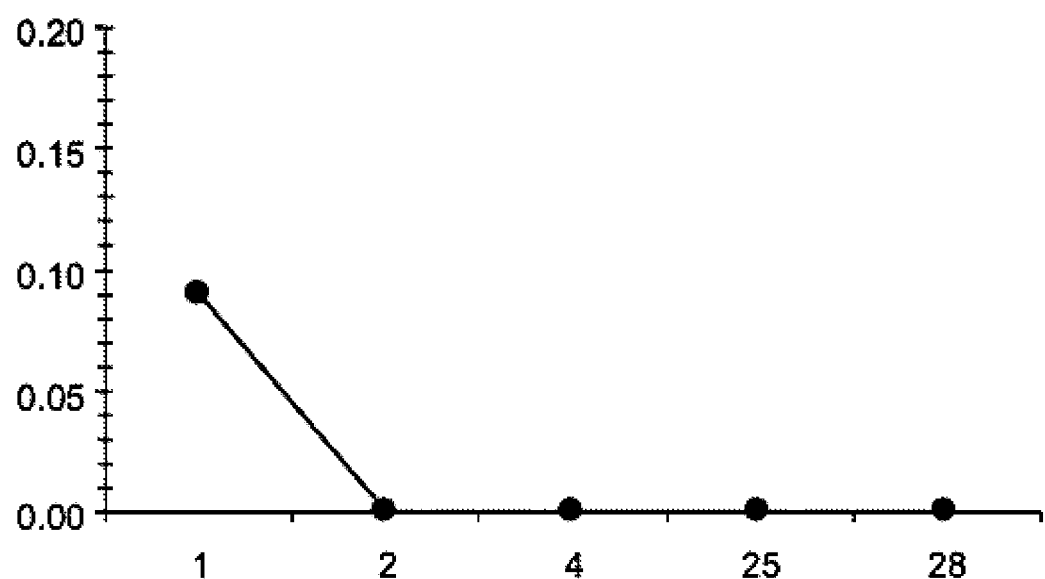
FIG. 1 shows the amount of dexamethasone in the anterior chamber following administration of a current commercial eye drop comprising 0.1% dexamethasone.
Figure 2:
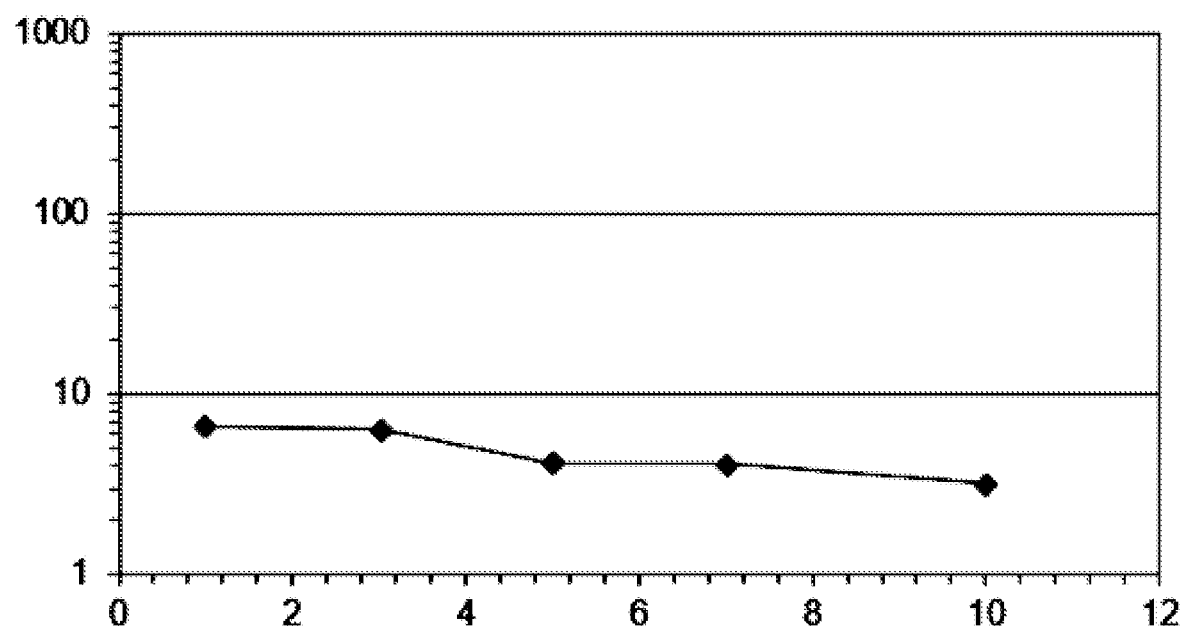
FIG. 2 shows the average amount of dexamethasone in the anterior chamber of rabbit eyes following instillation of an example of a liquid depot of the present embodiments comprising dexamethasone. X-axis, days; y-axis, dexamethasone ng/mL.

It should be understood that this invention is not limited to the particular methodology, protocols, and reagents, etc., described herein and as such may vary. The terminology used herein is for the purpose of describing particular embodiments only and is not intended to limit the scope of the present invention, which is defined solely by the claims.

All patents and other publications identified are incorporated herein by reference for the purpose of describing and disclosing, for example, the methodologies described in such publications that might be used in connection with the present invention but are not to provide definitions of terms inconsistent with those presented herein. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on information available to the applicants and do not constitute any admission as to the correctness of the dates or contents of these documents.

As used herein and in the claims, the singular forms "a," "an," and "the" include the plural reference unless the context clearly indicates otherwise. Throughout this specification, unless otherwise indicated, "comprise," "comprises" and "comprising" are used inclusively rather than exclusively, so that a stated integer or group of integers may include one or more other non-stated integers or groups of integers. The term "or" is inclusive unless modified, for example, by "either." Thus, unless context indicates otherwise, the word "or" means any one member of a particular list and also includes any combination of members of that list. Other than in the operating examples, or where otherwise indicated, all numbers expressing quantities of ingredients or reaction conditions used herein should be understood as modified in all instances by the term "about" which generally allows variation of ±1 unless context dictates otherwise. In general, and unless otherwise indicated or clarified by context, amounts or levels presented as "%" are based on weight (i.e., wt % or wt/wt).

Headings are provided for convenience only and are not to be construed to limit the invention in any way. Unless defined otherwise, all technical and scientific terms used herein have the same meaning as those commonly understood to one of ordinary skill in the art. The terminology used herein is for the purpose of describing particular embodiments only and is not intended to limit the scope of the present invention, which is defined solely by the claims. In order that the present disclosure can be more readily understood, certain terms are first defined. Additional definitions are set forth throughout the detailed description.

Ophthalmic formulations are needed for delivery of pharmaceutical agents on the eye, into the eye, or onto the conjunctiva of the eye. Currently available formulations used in ophthalmology include aqueous solutions, aqueous suspensions, ointments, and inserts. In current eye drop formulations, however, transcorneal transport (i.e., drug penetration into the eye) is not an effective process, as an estimated one-tenth of a dose penetrates into the eye. Moreover, current commercially available eye drops do not provide sustained release over extended periods of time, e.g., over the course of days. Accordingly, topical formulations that can effectively deliver pharmaceutical agents into tissues and fluids in the front of the eye clearly represent a long-felt but unmet need in the art.

More specifically, current commercially available ophthalmic solutions are aqueous based, and placed into the eye as eye drops. Current commercial solutions typically require instillation several times a day. Commercial ophthalmic aqueous eye drops require careful control of pH, buffer capacity, viscosity, and tonicity (osmotic pressure); particularly to avoid stinging upon application, which can lead to patient noncompliance. Current commercially available ophthalmic suspensions are also aqueous formulations but contain solid particles and typically produce a slightly longer effect than do solutions, but still require administration on a daily basis. Particle size is kept to a minimum to prevent irritation of the eye, but current aqueous suspensions are disadvantageous because of difficulty in avoiding particles large enough to irritate the eye; and these suspensions often cloud vision for an extended period of time after instillation. Current ophthalmic ointments are relatively difficult to apply and may distribute unevenly in the eye. Ointments remain in contact with the eye for an extended period compared with solutions or suspensions, producing a therapeutic effect of relatively longer duration, but this period is typically measured in hours, not days. Most ointments tend to blur patient vision as they remain viscous and are not removed easily by the tear fluid, which is a major disadvantage: ointments leave a film over the patient's eye that impairs the patient's vision for at least some time. Thus, ointments are generally used at night as adjunctive therapy to eye drops used during the day.

Ophthalmic solutions usually do not impair or interfere with vision (although initial instillation may yield fleeting blurry vision), but patients must forgo contact lenses and eye makeup whether using current solutions, suspensions, or ointments, and these factors also add to patient noncompliance with dosage regimen.

In addition to the considerations discussed above, ophthalmic products must remain sterile to prevent microbial contamination of the eye. Whether current ocular therapies are formulated as solution, suspension, or ointment, most current formulations are administered from droppers or tubes that must be used with care to avoid allowing the tip of the dropper or tube to touch the eyelid or any other surface that can contaminate the dispenser. Contamination of a dropper, solution, suspension, or the tip or cap of the tube can lead to serious eye infection. Accordingly, FDA Advisory Review Panel on OTC Ophthalmic Drug Products (1979) established preservatives and concentrations for use in formulations that will have direct contact with the eye. Many of these preservatives react with active agents or plastics, however, or increase irritation of the eye drops formulation.

In contrast to current commercially available ophthalmic formulations, the present embodiments provide a liquid depot that forms a film over the eye that is not blinked away and does not impair vision except fleetingly at the time of administration. The present embodiments provide a sustained-release liquid depot that can releases pharmaceutical agent(s) such that these agents can be detected for at least about 24 hours, at least about 36 hours, at least about 48 hours, at least about 60 hours, at least about 72 hours, at least about 7 days, at least about 14 days, or at least about 21 days, including intervals therebetween. It is unexpected, and indeed remarkable, that the active agent remains present in high enough concentrations to be therapeutically efficacious over the course of delivery. As shown in the Examples herein, after only a single application of liquid depot, pharmaceutical agent was detected in the tear film for at least 7 days and the liquid depot likely released drug for at least that long. Further, without being bound by theory, because the present depot delivers active agent to ocular tissues, some ocular tissues may become repositories from which drug is subsequently released, prolonging release or therapeutic benefit. Additionally, the liquid depot has a physical consistency that avoids running (compared with current aqueous drops) and allows the patient to wear contact lenses and eye makeup.

The present embodiments also advantageously provide instillation from a single-use dispenser such that preservative is not required in the formulation; because the present liquid depot provides sustained release and therapeutic benefit for at least 3 days, the liquid depot can be supplied in a single-administration dispenser that is easy to use because the patient (or health care provider) can focus all their attention to dispensing the formulation into the eye without diverting attention to avoiding all contact with the tip of the dispenser. Accordingly, at least one embodiment provides a single-use dispenser comprising the sustained-release liquid depot described herein, in which the dispenser is configured to deliver into an eye a single dose/dosage form of the liquid depot.

Additionally, oxygen sensitivity of many pharmaceutical agents results in instability. For this reason, current eye drops often include preservatives, such as sodium bisulfate, to increase stability of such active agents. The sustained-release liquid depot described herein is capable of releasing the active agent, at therapeutic levels, for at least about 24 hours, more preferably at least about 48 hours, and still more preferably at least about 72 hours, even though the depot is exposed to oxygen from atmospheric exposure and constant washing from fluids in the eye. It is unexpected that an active agent remains stable over the course of delivery, e.g., for at least 3 days. Without being bound by theory, this is likely due to the antioxidant nature of the tocopherol or tocotrienol excipient, which in the present embodiments is not unduly diluted or reduced by the presence of ocular film-forming excipient(s). Accordingly, in at least one embodiment, the sustained-release liquid depot comprises a biocompatible and biodegradable mixture of tocopherol or tocotrienol and an ocular film-forming excipient that has low solubility in aqueous solution.

In at least one embodiment, the sustained-release liquid depot comprises: about 60% to 90% (wt %) tocopherol (such as tocopheryl acetate), and about 10% to 40% (wt %) of an ocular film-forming excipient (such as decanoyl/octanoyl glycerides). In at least one embodiment, the liquid film-former excipient modulates (e.g., either increases or decreases) the viscosity of the liquid depot. In at least one embodiment, a liquid depot includes about 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, or about 90% (wt %), inclusive, or any interval therebetween, of tocopherol; and includes about 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, or about 40% (wt %), inclusive, or any interval therebetween, of ocular film-forming excipient. In one embodiment, the liquid depot comprises, consists, or consists essentially of (a) 10%-15% dexamethasone in (b) about 85%-90% (wt %) of a mixture of tocopheryl acetate: medium-chain triglycerides at a weight ratio of about 90:10 to about 60:40.

Regarding viscosity, this characteristic describes the resistance to deformation exhibited between molecules moving in a fluid, or a form of internal friction that resists a fluid's flow when stress is applied. The viscosity of a solution is often given in poise (P), centipoise (cP), or millipascal seconds (mPa s). For example, at 20° C. water has a viscosity of 1.00 mPa s, or 1.00 cP, whereas motor oil (SAE 40) has a viscosity of 319 mPa s. Many fluids exhibit less viscosity when heated: for example, at 25° C., water has a viscosity of 0.890 mPa s. See, e.g., Elert, PHYSICS HYPERTEXTBOOK (1998-2017). Generally, current aqueous-based eye drop solutions have viscosity ranging from 25 cP to 50 cP (at 20° C.); and some of these ophthalmic solutions may include viscosity enhancers added to increase viscosity and perhaps enable the solution to remain longer in the eye. Typical compounds added to enhance viscosity in current eye drops are available in various grades such as 15 cP, 100 cP, etc., and include methylcellulose, hydroxycellulose, hydroxypropylmethyl-cellulose, polyvinyl alcohol, and polyvinylpyrrolidone. In preferred embodiments, none of these viscous-enhancing compounds are included in the liquid depot described herein.

In one embodiment, a sustained-release liquid depot according to the subject invention consists of tocopheryl acetate, MIGLYOL®, and dexamethasone having a viscosity of 850 cP to 1100 cP, such as about 850, 851, 852, 853, 854, 855, 856, 857, 858, 859, 860, 899, 990, 994, 995, 996, 997, 998, 999, 1000, 1001, 1002, 1003, 1004, 1005, 1006, 1007, 1007, 1008, 1009, 1010, 1011, 1020, 1021, 1022, 1023, 1024, 1025, 1026, 1027, 1028, 1029, 1030, 1031, 1032, 1075, 1076, 1077, 1078, 1079, 1080, 1081, 1082, 1083, 1099, or 1100 cP, inclusive of any cP therebetween. In another embodiment, a sustained-release liquid depot, according to the subject invention, consists of tocopheryl acetate, MIGLYOL®, and dexamethasone having a viscosity of about 1027 cP. In another embodiment, a sustained-release liquid depot, according to the subject invention, consists of tocopheryl acetate, MIGLYOL®, and dexamethasone having a viscosity of 1027 cP±32 cP.

In at least one embodiment, the sustained-release liquid depot comprises, consists of, or consists essentially of a tocopherol and an ocular film-forming excipient. As used herein, "tocopherol" includes tocopherols, tocotrienols, esters thereof, and mixtures thereof. Tocopherol is commonly known as "vitamin E." Tocopherols and tocotrienols contain a chromanol ring and a hydrophobic side-chain of sixteen carbons. Depending on the pattern of methylation of the chromanol ring, these compounds exist as α-, β-, γ- and δ-tocopherols, each with a saturated side chain; or as α-, β-, γ- and δ-tocotrienols, each with a side chain containing three double bonds in the side chain. Tocopherols and tocotrienols can be extracted from a number of plant sources, such as palm oil. See, e.g., WO2014100327; Lee et al., *Methods for efficient analysis of tocopherols, tocotrienols & their metabolites in animal samples with HPLC-EC*, J. Food Drug Anal. 1-12 (2017). The tocopherol component of the present embodiments remains in liquid form in the depot and does not undergo phase shift to solid, crystalline, or liquid crystalline form upon contact with water or aqueous bodily fluids, e.g., tears. Tocopherols are highly viscous liquids, and their ability to flow at different conditions related to temperature and flow velocity is a fundamental property of tocopherols. The term "tocopherol" may be used herein to denote any of these liquid tocopherols or tocotrienols and derivatives thereof as provided herein and suitable for use as described herein.

In at least one embodiment, the tocopherol is tocopheryl acetate (also known as tocopherol acetate, vitamin E acetate, or "EA"), an ester of tocopherol and acetic acid. More specifically, tocopheryl acetate, IUPAC name "[(2R)-2,5,7,8-tetramethyl-2-[(4R,8R)-4,8,12-trimethyltridecyl]chroman-6-yl]acetate" (CAS Reg. No. 58-95-7), has low solubility in aqueous solution (having water solubility of <0.1 g/100 mL at 17° C.), a viscosity of 6.31 Pa s to 6.59 Pa s (20° C.), and a refractive index of 1.496 n20/D. By comparison, the average refractive index values of human tears are about 1.33698. Craig et al., *Refractive index & osmolality of human tears*, 72(10) Optom. Vis. Sci. 718-24 (1995). In one embodiment, the tocopherol is tocopheryl acetate. In at least one embodiment, the liquid depot comprises any amount from 60% to 90%, inclusive, such as 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89% or 90% (wt %), tocopheryl acetate.

In addition to a tocopherol, the sustained-release liquid depot described herein includes an additional ocular film-former excipient, which in general terms is an excipient that is biocompatible and safe to use in the human eye, has low solubility in aqueous solution, does not impair vision (e.g., has a suitable refractive index at least in combination with tocopherol), and does not adversely affect either tocopherol stability in the eye or release of the pharmaceutical agent(s) from the liquid depot. It should be understood that although tocopherol is generally capable of forming a film in the eye and providing sustained release, tocopherol is too viscous for practical use in the liquid depot described herein; the ocular film-forming excipient improves the spreadability or hastens the application of the liquid depot described herein. In general, the ocular film-forming excipient renders the tocopherol less viscous. In other words, compared with tocopherol (e.g., tocopheryl acetate) as the sole component of a liquid depot, the additional ocular film-forming component provides a liquid depot that is comparatively less sticky, tacky, or viscous. This ocular film-forming excipient facilitates rapid and smooth coverage over the cornea, and also modifies the viscosity of the tocopherol component (e.g., tocopheryl acetate). It should be noted, however, that inclusion of too much film-forming agent results in insufficient film depot and increases flushing of the active agent(s) from the eye.

Generally speaking, the ratio of tocopherol:film-forming excipient (e.g., wt/wt ratio) can be adjusted to modulate (e.g. either increase or decrease) the sustained release profile of the liquid depot. For example, decreasing the amount of film-forming excipient generally increases the time in which the liquid depot stays in the eye and delivers active agent(s), i.e., increases the sustained release profile. Alternatively, or additionally, depending on the indication, the sustained release profile can be extended by increasing the amount of active agent(s) in the liquid depot. Further, depending on the indication, the concentration of active agent can be increased to increase the amount of active agent that is delivered to the front of the eye, e.g., the cornea, by the liquid depot.

Use of particular ocular film-forming excipients and the amount of each additional ocular film-former included in the sustained-release liquid depot described herein has been determined through laborious and detailed experiments to provide the type of excipient with the required characteristics and the amount needed to provide non-stick, nearly immediate coating over the cornea with sufficient tocopherol to provide sustained release of pharmaceutical agent from the liquid depot. The required beneficial characteristics of the ocular film-forming excipient include safety for use in the eye, chemical and physical stability over a long period of time, chemical compatibility with other formulation components, solubility in the formulation, ability to enhance the sustained release of the pharmaceutically active component, inertness, and the diffusion away from the liquid depot after exerting the desired effects.

Many potential film-forming excipients were considered or evaluated for inclusion in the liquid depot of the present embodiments, including castor oil, corn oil, triacetin, tributyrin, tricaprin, tricaprylin, water, Dermol esters (e.g., isononyl isononanoate), BENZOFLEX™ (plasticizer), polyethylene and polypropylene glycols, long chain aliphatic alcohols, hydroxypropyl methyl cellulose (HPMC), stearic acids, and stearic esters. These carriers were found to lack at least one of the multiple beneficial characteristics needed in order to progress through the rigorous evaluation processes employed to arrive at the liquid depot described herein. These excipients are not included in the liquid depot described herein.

In at least one embodiment, the ocular film-forming excipient is a mixture of triglycerides. In at least one embodiment, the ocular film-forming excipient is one or more medium-chain triglycerides (MCT). For example, mixed decanoyl and octanoyl glycerides (e.g., CAS No. 73398-61-5), comprise >95% saturated fatty acid chains, and are transparent, colorless or slightly yellow liquids, immiscible in water, practically odorless and tasteless, specific gravity of 0.94-0.96 (20° C.), refractive index of 1.440 to 1.452 n20D (20° C.), and viscosity ranging from 24 mPa s to 33 mPa s (20° C.) (14.9 cSt at 100° C.). Synonyms for MCT include ecanoyl/octanoyl glycerides, mixed decanoate and octanoate triglycerides, glyceryl tricaprylate/caprate, oleum neutrale, Bergabest, Captex® 300, Captex® 355, Crodamol® GTCC/C, Labrafac® CC, MCT oil, MIGLYOL® 810, MIGLYOL® 812, Myritol®, Neobee® M5, Nesatol®, or Waglinol® 3/9280. Accordingly, film-formers may also be referred to as triglycerides (and triglyceride-like) excipients, that include decanoyl/octanoyl glycerides (such as MIGLYOL® 810), caprylic/capric triglyceride (e.g., MIGLYOL® 812), and propylene glycol dicaprylate/dicaprate (triglyceride like) (e.g., MIGLYOL® 840), and mixtures thereof.

In exemplary embodiments, MIGLYOL®, when combined with tocopherol, imparts beneficial sustained release characteristics to the liquid depot described herein: such as beneficial modulation of viscosity, flowability, inertness, transparency, solubility with other components, and permeability.

Accordingly, in one embodiment, the film-forming excipient is immiscible or has low solubility in water or aqueous solution. In one embodiment, the film-forming excipient has a viscosity of 27 mPa s to 33 mPa s (20° C.), inclusive, such as about 27, 28, 29, 30, 31, 32, or about 33 mPa s (20° C.), including intervals therebetween. In one embodiment, the film-forming excipient has a refractive index of 1.448 n20D to 1.451 n20D, such as about 1.448, 1.449, 1.450, or about 1.451 n20D, or intervals therebetween. In one embodiment, the film-forming excipient comprises, consists of, or consists essentially of decanoyl/octanoyl glycerides. In one embodiment, the decanoyl/octanoyl glycerides excipient is at least one of MIGLYOL® 810 or MIGLYOL® 812. In at least one embodiment, the liquid depot includes any amount from 10% to 30%, inclusive, decanoyl/octanoyl glycerides, such as MIGLYOL® 810 or MIGLYOL® 812.

The liquid depot, when lacking a pharmaceutical agent (i.e., before an agent is loaded into the depot) may also be referred to as a blank, control, excipient component of a formulation, biodegradable excipient, excipient mixture, vehicle, and the like. The liquid depot remains in liquid state under physiologic conditions, both in vitro and in vivo, and does not polymerize or become solid after placement in the eye. This liquid depot can be loaded with highly concentrated active agent, but nevertheless remains liquid, safe and effective, while reducing side effects normally associated with the active agent administered in traditional eye drop formulations. Loading refers to any means by which at least one active agent is dispersed, dissolved, mixed, suspended, or otherwise incorporated into the liquid depot. Liquid refers generally to fluids, but also includes suspensions of solids dispersed in liquids (dispersions, suspensions, colloidal mixtures), and gasses dissolved in or otherwise present together within liquids, wherein fluidity of the liquid is maintained. The liquid depot of the present embodiments retains its fluid nature (i.e., does not solidify) before and after placement in the eye, and remains fluid as it biodegrades over time. In at least one embodiment, the liquid depot does not contain a pharmaceutical agent, and when instilled into the eye provides a liquid "bandage" or eye band aid useful for a variety of maladies including inflammation or eye protection.

In at least one embodiment, a single administration of the liquid depot, such as instillation of a liquid depot of about 20 $\mu m^3$ (20 µL) to about 70 $\mu m^3$ (70 µL) (such as about 20 µL, 25 µL, 30 µL, 35 µL, 40 µL, 45 µL, 50 µL, 55 µL, 60 µL, 65 µL, or about 70 µL, including intervals therebetween) provides for sustained release of a pharmaceutical agent to an interior tissue of the eye for at least about 24 hours, at least about 48 hours, at least about 72 hours, at least about 4 days, at least about 5 days, at least about 6 days, at least about 1 week (7 days), at least about 2 weeks (14 days), or at least about 3 weeks (21 days), including intervals therebetween. In at least one embodiment, a single instillation of the liquid depot, such as a liquid depot of about 20 $\mu m^3$ (20 µL) to about 70 $\mu m^3$ (70 µL), inclusive and including intervals therebetween, provides for sustained release of active agent to an interior tissue of the eye for a period of at least about 24 hours, at least about 48 hours, at least about 72 hours, at least about 4 days, at least about 7 days (1 week), at least about 2 weeks, or at least about 3 weeks, including intervals therebetween. It should further be understood that a single instillation might include two micro-drops (e.g., of 25 µL) instilled in rapid succession to provide a single one-time dose (e.g., of 50 µL).

Many pharmaceutical agents are suitable for sustained release from the liquid depot described herein. Such agents may have low solubility in water or aqueous solutions. In some embodiments, active agents are more stable in the liquid depot compared with the stability of those active agents in current aqueous-based eye drop formulations.

It should be noted that, without being bound by theory, it appears that the efficiency with which the liquid depot delivers active agents to ocular tissues allows some tissues to retain agents after the depot film has dissipated, extending release from such tissues or benefit to such tissues after the liquid depot is gone.

References to "pharmaceutical agent," "pharmaceutically active," "pharmaceutical," "drug," "medicament," "active agent," "active drug," "bioactive agent" or "therapeutic agent" and the like, refer in a general sense to substances useful in the medical and scientific arts, including, for example, drugs, biologics, diagnostic agents (e.g, dyes or contrast agents) or other substances used for therapeutic, preventative, diagnostic, or research purposes. Example pharmaceutical agents include biologics (e.g., insulin), chemotherapeutic agents, small molecules, antigens, interferons, polyclonal or monoclonal antibodies, anesthetics, interfering RNAs, gene vectors, contrast agents, or combinations of any of these. Reference to general or specific pharmaceutical agents or drugs includes pharmaceutically acceptable analogues, derivative, and salts thereof. For example, reference to ketotifen includes ketotifen fumarate. Active agents that may be included in the liquid depots described herein are provided, for example, in U.S. Pat. No. 9,011,915.

"Inactive" substances typically refer to carriers, excipients, diluents, and the like, which are well-known in the art, although such substances may have beneficial function, such as, for example, stabilizing a pharmaceutical agent.

Typically, pharmaceutical agents are administered to the eye to have relatively local effects such as miosis, mydriasis, and anesthesia, or to reduce intraocular pressure (IOP) in treating glaucoma. Without being bound by theory, because the liquid depot formulations described herein deliver active agents to ocular tissues, in some instances such ocular tissues retain active agent after the depot is no longer evident in the tear film, further providing sustained release of the active agent.

In at least one embodiment, an active agent is delivered to the eye in a manner that provides treatment or prevention (e.g., prophylaxis) of ocular disease in the front of the eye. In some embodiments, the front of the eye is the surface of the eye. In some embodiments, the front of the eye includes the ocular tissue and fluids in the front of the eye including aqueous humor, cornea, conjunctiva, and iris/ciliary body. Regarding the surface of the eye, the present embodiments provide for treatment or prevention of maladies associated with the surface of the eye, including conjunctivitis, allergy, acute dry eye, dry eye, irritation, or infection. In some embodiments, delivery of the active agent from the sustained-release liquid depot provided herein is intermittent, e.g., once every 1, 2, 3, 4, 5, 6, 7, 8, 9, or 10 days, once every 2 weeks, or once every 3 weeks.

In one embodiment, an active agent is delivered to the eye in a manner that provides treatment or prevention (e.g., prophylaxis) of ocular disease in the front of the eye (anterior), while, optionally, concurrently treating or preventing ocular disease in the back of the eye (posterior).

In at least one embodiment, one application of the sustained-release liquid depot delivers active agent(s) to the front of the eye for at least 3 days. In at least one embodiment, one application of the sustained-release liquid depot delivers active agent(s) to the front of eye for at least 7 days. In at least one embodiment, one application of the sustained-release liquid depot delivers active agent(s) to the front of eye for at least 14 days.

In another aspect, methods of managing a clinical condition associated with or affecting front of the eye are provided, comprising the intermittent administration (e.g., once every 3, 4, 5, 6, 7, 8, 9 or 10 days, once every 2 weeks, or once every 3 weeks) of a single dose of a medicament-containing liquid depot as described herein, wherein the dose is about 20 μL to about 70 μL, inclusive and including volumes therebetween. It should be understood that reference to intermittent dosage regimens reflects therapeutic dose over an extended period of time, such that administering once every three days or longer implies that sustained release has provided therapeutic effect such that more frequent administration is not indicated.

In one embodiment, the clinical condition is inflammation. In one embodiment, the clinical condition is allergy. In one embodiment, the clinical condition is infection. In one embodiment, the clinical condition is intraocular pressure or glaucoma. In one embodiment, the clinical condition is uveitis. It should be understood, however, that these indications may not be mutually exclusive; for example, infection is often associated with inflammation. Similarly, anti-infectives such as cyclosporine, are often administered to reduce inflammation. Accordingly, at least one embodiment provides a liquid depot formulation for prophylaxis of infection and inflammation, such as, for example, blepharitis, or inflammatory meibomian gland disease.

Another aspect of the present embodiments provides a method of treating a disease or malady of the eye, such as infection, corneal abrasion or other trauma to the eye surface, blepharitis, inflammatory meibomian gland disease, meibomian gland dysfunction, allergic conjunctivitis, chronic conjunctivitis, Sjögren's syndrome, dry eye (keratoconjunctivitis sicca), aqueous-deficient dry eye, mucin-deficient dry eye (punctate epithelial keratitis), episcleritis, keratitis (corneal ulcers), pterigia, Stevens-Johnson syndrome, ocular citatrical pemphigoid/mucous membrane pemphigoid, irregular cornea condition or other surface abnormalities, epitheliopathy, neurotrophic cornea, corneal dystrophy such as Fuch's dystrophy, peripheral or marginal degeneration of the cornea, conjunctivochalasis, glaucoma, conjunctival degeneration such as pinguecula, pingueculitis, or re-epithelialization of corneal epithelial defects in patients who have undergone photorefractive keratectomy.

In some embodiments, the sustained-release liquid depot comprises, as the pharmaceutical agent, a bioactive or therapeutic agent. Bioactive or therapeutic agents may have more than one activity or benefit, hence the following embodiments are not mutually exclusive. For example, anti-inflammatory steroids may have angiostatic activity as well. In some embodiments, the sustained-release liquid depot comprises at least one anti-inflammatory agent. In some embodiments, the sustained-release liquid depot comprises at least one anti-allergy agent. In some embodiments, the sustained-release liquid depot comprises at least one anti-infective. In some embodiments, the sustained-release liquid depot comprises at least one anti-glaucoma therapy.

In another embodiment, the sustained-release liquid depot contains two or more different active agents, wherein each active agent selected for its ability to either stay associated with the cornea or pass through the cornea, such that one active agent stays on or in the cornea and the other active agent penetrates the interior of the eye. In one embodiment, the liquid depot includes two or more active agents with similar capacities to penetrate the eye.

At least one embodiment provides a liquid depot that releases anti-allergy therapy, such as antihistamine or mast cell stabilizer. Exemplary anti-allergy agents used to treat allergies/itchy eyes include, for example, ketotifen, ketotifen fumarate, lodoxamine, azelastine, olopatadine, or epinastine, or combinations thereof.

Accordingly, a specific embodiment is a liquid depot comprising tocopherol, ocular film-forming excipient, and ketotifen. An exemplary embodiment includes about 70% to 80% (wt %) tocopherol (such as tocopheryl acetate), about 10% to 30% (wt %) ocular film-forming excipient, such as decanoyl/octanoyl glycerides (e.g., MIGLYOL®), and ketotifen.

Another specific embodiment is a liquid depot comprising tocopherol, ocular film-forming excipient, and lodoxamine. An exemplary embodiment includes about 70% to 80% (wt %) tocopherol (such as tocopheryl acetate), about 10% to 30% (wt %) ocular film-forming excipient, such as decanoyl/octanoyl glycerides (e.g., MIGLYOL®), and lodoxamine.

Another specific embodiment is a liquid depot comprising tocopherol, ocular film-forming agent, and azelastine. An exemplary embodiment includes about 70% to 80% (wt %) tocopherol (such as tocopheryl acetate), about 10% to 30% (wt %) ocular film-forming excipient, such as decanoyl/octanoyl glycerides (e.g., MIGLYOL®), and azelastine.

Another specific embodiment is a liquid depot comprising tocopherol, ocular film-forming excipient, and olopatadine. An exemplary embodiment includes about 70% to 80% (wt %) tocopherol (such as tocopheryl acetate), about 10% to 30% (wt %) ocular film-forming excipient, such as decanoyl/octanoyl glycerides (e.g., MIGLYOL®), and olopatadine.

Yet another specific embodiment is a liquid depot comprising tocopherol, ocular film-forming excipient, and epinastine. An exemplary embodiment includes about 70% to 80% (wt %) tocopherol (such as tocopheryl acetate), about 10% to 30% (wt %) ocular film-forming excipient, such as decanoyl/octanoyl glycerides (e.g., MIGLYOL®), and epinastine.

At least one embodiment provides a liquid depot that releases anti-glaucoma therapy. Anti-glaucoma active agents include inflow-suppressing/inhibiting agents, such as beta blocking agents (e.g., timolol, betaxolol, carteolol, levobunolol, etc.), topical carbonic anhydrase inhibitors (e.g., dorzolamide, brinzolamide), sympathomimetics (e.g., epinephrine, dipivefrin, clonidine, apraclonidine, brimonidine), outflow-facilitating agents including parasympathomimetics (e.g., cholinergic agonists such as pilocarpine), and prostaglandin analogues and related compounds (e.g., latanoprost, travoprost, bimatoprost, unoprostone, or tafluprost). Different pharmaceutical agents can be used alone or in combination to reduce intraocular pressure, including, for example, bimatoprost, latanoprost, travaprost, tafluprost, brimonidine, betaxolol, levobunolol, metipranolol, or timolol.

Accordingly, a specific embodiment is a liquid depot comprising tocopherol, ocular film-forming excipient, and timolol. An exemplary embodiment includes about 70% to 80% (wt %) tocopherol (such as tocopheryl acetate), about 10% to 30% (wt %) ocular film-forming excipient, such as decanoyl/octanoyl glycerides (e.g., MIGLYOL®), and timolol.

Another specific embodiment is a liquid depot comprising tocopherol, ocular film-forming agent, and betaxolol. An exemplary embodiment includes about 70% to 80% (wt %) tocopherol (such as tocopheryl acetate), about 10% to 30% (wt %) ocular film-forming excipient, such as decanoyl/octanoyl glycerides (e.g., MIGLYOL®), and betaxolol.

Another specific embodiment is a liquid depot comprising tocopherol, ocular film-forming agent, and carteolol. An exemplary embodiment includes about 70% to 80% (wt %) tocopherol (such as tocopheryl acetate), about 10% to 30% (wt %) ocular film-forming excipient, such as decanoyl/octanoyl glycerides (e.g., MIGLYOL®), and carteolol.

Another specific embodiment is a liquid depot comprising tocopherol, ocular film-forming agent, and levobunolol. An exemplary embodiment includes about 70% to 80% (wt %) tocopherol (such as tocopheryl acetate), about 10% to 30% (wt %) ocular film-forming excipient, such as decanoyl/octanoyl glycerides (e.g., MIGLYOL®), and levobunolol.

Another specific embodiment is a liquid depot comprising tocopherol, ocular film-forming agent, and dorzolamide. An exemplary embodiment includes about 70% to 80% (wt %) tocopherol (such as tocopheryl acetate), about 10% to 30% (wt %) ocular film-forming excipient, such as decanoyl/octanoyl glycerides (e.g., MIGLYOL®), and dorzolamide.

Another specific embodiment is a liquid depot comprising tocopherol, ocular film-forming agent, and brinzolamide. An exemplary embodiment includes about 70% to 80% (wt %) tocopherol (such as tocopheryl acetate), about 10% to 30% (wt %) ocular film-forming excipient, such as decanoyl/octanoyl glycerides (e.g., MIGLYOL®), and brinzolamide.

Another specific embodiment is a liquid depot comprising tocopherol, ocular film-forming agent, and epinephrine. An exemplary embodiment includes about 70% to 80% (wt %) tocopherol (such as tocopheryl acetate), about 10% to 30% (wt %) ocular film-forming excipient, such as decanoyl/octanoyl glycerides (e.g., MIGLYOL®), and epinephrine.

Another specific embodiment is a liquid depot comprising tocopherol, ocular film-forming agent, and dipivefrin. An exemplary embodiment includes about 70% to 80% (wt %) tocopherol (such as tocopheryl acetate), about 10% to 30% (wt %) ocular film-forming excipient, such as decanoyl/octanoyl glycerides (e.g., MIGLYOL®), and dipivefrin.

Another specific embodiment is a liquid depot comprising tocopherol, ocular film-forming agent, and clonidine. An exemplary embodiment includes about 70% to 80% (wt %) tocopherol (such as tocopheryl acetate), about 10% to 30% (wt %) ocular film-forming excipient, such as decanoyl/octanoyl glycerides (e.g., MIGLYOL®) and clonidine.

Another specific embodiment is a liquid depot comprising tocopherol, ocular film-forming agent, and apraclonidine. An exemplary embodiment includes about 70% to 80% (wt %) tocopherol (such as tocopheryl acetate), about 10% to 30% (wt %) ocular film-forming excipient, such as decanoyl/octanoyl glycerides (e.g., MIGLYOL®), and apraclonidine.

Another specific embodiment is a liquid depot comprising tocopherol, ocular film-forming agent, and brimonidine. An exemplary embodiment includes about 70% to 80% (wt %) tocopherol (such as tocopheryl acetate), about 10% to 30% (wt %) ocular film-forming excipient, such as decanoyl/octanoyl glycerides (e.g., MIGLYOL®), and brimonidine.

Another specific embodiment is a liquid depot comprising tocopherol, ocular film-forming agent, and pilocarpine. An exemplary embodiment includes about 70% to 80% (wt %) tocopherol (such as tocopheryl acetate), about 10% to 30% (wt %) ocular film-forming excipient, such as decanoyl/octanoyl glycerides (e.g., MIGLYOL®), and pilocarpine.

Another specific embodiment is a liquid depot comprising tocopherol, ocular film-forming agent, and latanoprost. An exemplary embodiment includes about 70% to 80% (wt %) tocopherol (such as tocopheryl acetate), about 10% to 30% (wt %) ocular film-forming excipient, such as decanoyl/octanoyl glycerides (e.g., MIGLYOL®), and latanoprost.

Another specific embodiment is a liquid depot comprising tocopherol, ocular film-forming agent, and travoprost. An exemplary embodiment includes about 70% to 80% (wt %) tocopherol (such as tocopheryl acetate), about 10% to 30% (wt %) ocular film-forming excipient, such as decanoyl/octanoyl glycerides (e.g., MIGLYOL®), and travoprost.

Another specific embodiment is a liquid depot comprising tocopherol, ocular film-forming agent, and bimatoprost. An exemplary embodiment includes about 70% to 80% (wt %) tocopherol (such as tocopheryl acetate), about 10% to 30% (wt %) ocular film-forming excipient, such as decanoyl/octanoyl glycerides (e.g., MIGLYOL®), and bimatoprost.

Another specific embodiment is a liquid depot comprising tocopherol, ocular film-forming agent, and unoprostone. An exemplary embodiment includes about 70% to 80% (wt %) tocopherol (such as tocopheryl acetate), about 10% to 30% (wt %) ocular film-forming excipient, such as decanoyl/octanoyl glycerides (e.g., MIGLYOL®), and unoprostone.

Yet another specific embodiment is a liquid depot comprising tocopherol, ocular film-forming agent, and tafluprost. An exemplary embodiment includes about 70% to 80% (wt %) tocopherol (such as tocopheryl acetate), about 10% to 30% (wt %) ocular film-forming excipient, such as decanoyl/octanoyl glycerides (e.g., MIGLYOL®), and tafluprost.

At least one embodiment provides a sustained-release liquid depot that releases anti-inflammatory therapy, such as nonsteroidal anti-inflammatory drugs (NSAIDs), or steroidal anti-inflammatory, e.g., corticosteroids. The embodiments described herein support use of the liquid depot for a breadth of clinical indications for which anti-inflammatories are used. For example, although true anti-histamines are often used as anti-allergy eye drops, anti-inflammatories, including, e.g., loteprednol, are also used to alleviate allergies. For example, corticosteroids are used to treat allergic conjunctivitis. Indeed, the sustained-release liquid depot formulations comprising anti-inflammatory medicines as described herein may find clinical application in many different clinical indications, e.g., in treating or preventing: (a) conjunctivitis, (b) dry eye, (c) inflammation associated with ocular surgery, including but not limited to, cataract surgery and vitrectomy, (d) allergy, (e) itchy eyes, (f) uveitis, (g) blepharitis, or (h) inflammatory meibomian gland disease.

Accordingly, at least one embodiment provides a method of treating ocular inflammation comprising instilling into the eye of a patient in need thereof a sustained-release liquid depot comprising, consisting, or consisting essentially of anti-inflammatory agent, tocopherol, and MCT (decanoyl/octanoyl glycerides). In some embodiments, the anti-inflammatory agent is a corticosteroid, the tocopherol is tocopheryl acetate, and the MCT is MIGLYOL®. In a particular embodiment, the liquid depot consists of 10% (wt %) dexamethasone, 72% (wt %) tocopheryl acetate, and 18% (wt %) MIGLYOL®, and dexamethasone is released for at least 7 days.

At least one embodiment provides a method of treating ocular infection comprising instilling into the eye of a patient in need thereof a sustained-release liquid depot comprising, consisting, or consisting essentially of anti-infective agent, tocopherol, and MCT (decanoyl/octanoyl glycerides). In some embodiments, the anti-infective agent is a quinolone antibiotic, the tocopherol is tocopheryl acetate, and the MCT is MIGLYOL®. In a particular embodiment, the liquid depot consists of 15% (wt %) moxifloxacin suspended, mixed, or dissolved in 85% (wt %) of a mixture of 70% (wt %) tocopheryl acetate and 30% (wt %) MIGLYOL®, and moxifloxacin is released for at least 7 days. In a particular embodiment, the liquid depot consists of 20% (wt %) moxifloxacin suspended, mixed, or dissolved in 80% (wt %) of a mixture of 70% (wt %) tocopheryl acetate and 30% (wt %) MIGLYOL®, and moxifloxacin is released for at least 7 days.

In at least one embodiment, the liquid depot includes a corticosteroid anti-inflammatory, such as, for example, dexamethasone, prednisolone, prednisone, loteprednol, triamcinolone, or fluorometholone or combinations thereof. Other anti-inflammatory agents are known in the art.

Accordingly, a specific embodiment is a liquid depot comprising tocopherol, ocular film-forming agent, and dexamethasone. An exemplary embodiment includes about 70% to 80% (wt %) tocopherol (such as tocopheryl acetate), about 10% to 30% (wt %) ocular film-forming excipient, such as decanoyl/octanoyl glycerides (e.g., MIGLYOL®), and dexamethasone.

Another specific embodiment is a liquid depot comprising tocopherol, ocular film-forming agent, and prednisolone. An exemplary embodiment includes about 70% to 80% (wt %) tocopherol (such as tocopheryl acetate), about 10% to 30% (wt %) ocular film-forming excipient, such as decanoyl/octanoyl glycerides (e.g., MIGLYOL®), and prednisolone.

Another specific embodiment is a liquid depot comprising tocopherol, ocular film-forming agent, and prednisone. An exemplary embodiment includes about 70% to 80% (wt %) tocopherol (such as tocopheryl acetate), about 10% to 30% (wt %) ocular film-forming excipient, such as decanoyl/octanoyl glycerides (e.g., MIGLYOL®), and prednisone.

Another specific embodiment is a liquid depot comprising tocopherol, ocular film-forming agent, and loteprednol. An exemplary embodiment includes about 70% to 80% (wt %) tocopherol (such as tocopheryl acetate), about 10% to 30% (wt %) ocular film-forming excipient, such as decanoyl/octanoyl glycerides (e.g., MIGLYOL®), and loteprednol.

Accordingly, a specific embodiment is a liquid depot comprising tocopherol, ocular film-forming agent, and fluorometholone. An exemplary embodiment includes about 70% to 80% (wt %) tocopherol (such as tocopheryl acetate), about 10% to 30% (wt %) ocular film-forming excipient, such as decanoyl/octanoyl glycerides (e.g., MIGLYOL®), and fluorometholone.

As noted above, anti-infectives such as cyclosporine are often administered to reduce inflammation. Accordingly, in at leas one embodiment, the liquid depot comprises cyclosporine. An exemplary embodiment includes about 70% to 80% (wt %) tocopherol (such as tocopheryl acetate), about 10% to 30% (wt %) ocular film-forming excipient, such as decanoyl/octanoyl glycerides (e.g., MIGLYOL®), and cyclosporine.

In at least one embodiment, the liquid depot comprises a non-steroidal anti-inflammatory agent (NSAID), such as, for example, ketorolac, nepafenac, bromfenac, or diclofenac, or combinations thereof.

Accordingly, in one embodiment, the liquid depot contains tocopherol, ocular film-forming excipient, and ketorolac. An exemplary embodiment includes about 70% to 80% (wt %) tocopherol (such as tocopheryl acetate), about 10% to 30% (wt %) ocular film-forming excipient, such as decanoyl/octanoyl glycerides (e.g., MIGLYOL®), and ketorolac.

In one embodiment, the liquid depot contains tocopherol, ocular film-forming agent, and nepafenac. An exemplary embodiment includes about 70% to 80% (wt %) tocopherol (such as tocopheryl acetate), about 10% to 30% (wt %) ocular film-forming excipient, such as decanoyl/octanoyl glycerides (e.g., MIGLYOL®), and nepafenac.

In another embodiment, the liquid depot contains tocopherol, ocular film-forming agent, and bromfenac. An exemplary embodiment includes about 70% to 80% (wt %) tocopherol (such as tocopheryl acetate), about 10% to 30% (wt %) ocular film-forming excipient, such as decanoyl/octanoyl glycerides (e.g., MIGLYOL®), and bromfenac.

In yet another embodiment, the liquid depot contains tocopherol, ocular film-forming agent, and diclofenac. An exemplary embodiment includes about 70% to 80% (wt %) tocopherol (such as tocopheryl acetate), about 10% to 30% (wt %) ocular film-forming excipient, such as decanoyl/octanoyl glycerides (e.g., MIGLYOL®), and diclofenac.

At least one embodiment provides a liquid depot for the sustained release of anti-infectives useful in treating or preventing topical ocular or intraocular infections. In at least one embodiment, the liquid depot comprises an anti-infective such as, for example, moxifloxacin, gatifloxacin, levofloxacin, ciprofloxacin, gentamicin, tobramycin, or chloramphenicol, or combinations thereof.

Accordingly, in one embodiment, the liquid depot contains tocopherol, ocular film-forming excipient, and moxifloxacin. An exemplary embodiment contains 10%-30% (wt %) moxifloxacin in 70%-90% (wt %) of a mixture of 65%-90% (wt %), tocopherol (such as tocopheryl acetate) and 10%-35% (wt %) ocular film-forming excipient, such as decanoyl/octanoyl glycerides (e.g., MIGLYOL®). In other words, an embodiment of a moxifloxacin liquid depot for the sustained release of moxifloxacin contains 10%-30% (wt %) moxifloxacin, 58.5%-81% tocopherol, and 9%-31.5% film-forming excipient. In another embodiment, the liquid depot contains 15%-20% (wt %) moxifloxacin in 80%-85% (wt %) of a mixture of 65%-90% (wt %), tocopherol (such as tocopheryl acetate) and 10%-35% (wt %) ocular film-forming excipient, such as decanoyl/octanoyl glycerides (e.g., MIGLYOL®).

In one embodiment, the liquid depot contains tocopherol, ocular film-forming agent, and gatifloxacin. An exemplary embodiment includes 10%-30% (wt %) gatifloxacin in 70%-90% (wt %) of a mixture of 65%-90% (wt %) tocopherol (such as tocopheryl acetate) and 10%-35% (wt %) ocular film-forming excipient, such as decanoyl/octanoyl glycerides (e.g., MIGLYOL®).

In one embodiment, the liquid depot contains tocopherol, ocular film-forming excipient, and levofloxacin. An exemplary embodiment contains levofloxacin in 70%-90% (wt %) of a mixture of about 65% to about 90% (wt %), inclusive, tocopherol (such as tocopheryl acetate), and about 10% to about 35% (wt %), inclusive, ocular film-forming excipient, such as decanoyl/octanoyl glycerides (e.g., MIGLYOL®).

In one embodiment, the liquid depot contains tocopherol, ocular film-forming agent, and ciprofloxacin. An exemplary embodiment includes about 70% to 80% (wt %) tocopherol (such as tocopheryl acetate), about 10% to 30% (wt %) ocular film-forming excipient, such as decanoyl/octanoyl glycerides (e.g., MIGLYOL®), and ciprofloxacin.

In another embodiment, the liquid depot contains tocopherol, ocular film-forming agent, and gentamycin. An exemplary embodiment includes about 70% to 80% (wt %) tocopherol (such as tocopheryl acetate), about 10% to 30% (wt %) ocular film-forming excipient, such as decanoyl/octanoyl glycerides (e.g., MIGLYOL®), and gentamycin.

In one embodiment, the liquid depot contains tocopherol, ocular film-forming agent, and tobramycin. An exemplary embodiment includes about 70% to 80% (wt %) tocopherol (such as tocopheryl acetate), about 10% to 30% (wt %) ocular film-forming excipient, such as decanoyl/octanoyl glycerides (e.g., MIGLYOL®), and tobramycin.

In yet another embodiment, the liquid depot contains tocopherol, ocular film-forming agent, and chloramphenicol. An exemplary embodiment includes about 70% to 80% (wt %) tocopherol (such as tocopheryl acetate), about 10% to 30% (wt %) ocular film-forming agent, such as fatty acid ester(s) (e.g., decanoyl/octanoyl glycerides), and chloramphenicol.

At least one embodiment provides a liquid depot formulation for prophylaxis of infection and inflammation, such as cystoid macular edema (CME) or uveitis (both of which may be associated with cataract surgery), blepharitis, and Inflammatory Meibomian Gland Disease.

Regarding uveitis, the uvea is the middle layer of the eye that contains much of the eye's blood vessels in addition to the iris, ciliary body, and choroid. Uveitis is a potentially blinding inflammation of this tissue, which disrupts vision by causing problems with the lens, retina, optic nerve, and vitreous. Uveitis can be anterior, intermediate, posterior or pan-uveitis, and is typically treated with steroids to reduce inflammation. A study comparing oral corticosteroids (prednisone) with a surgically implanted sustained release corticosteroid (0.59 mg fluocinolone acetonide intra-vitreous implant) revealed that although both treatments decreased inflammation in the eye, the corticosteroid implant produced more eye problems, such as cataracts, abnormally high intraocular pressure (IOP≥21 mmHg), and glaucomatous optic nerve damage. Indeed, 69% of patients assigned to the implant required IOP lowering therapy, versus 26% of the systemic group; 15% versus 3% had an IOP spike to at least 40 mmHg; 23% versus 6% developed glaucomatous optic nerve damage; and 32% versus 5% required a surgical intervention. Importantly, the study concluded that IOP elevations in a substantial proportion of implanted patients would not be controllable with current eye drops therapy. Friedman et al., *Risk of elevated intraocular pressure and glaucoma in patients with uveitis; results of the Multicenter Uveitis Steroid Treatment Trial,* 120(8) Ophthalmol. 1571-79 (2013).

Regarding cataract, characterized by the development of lenticular opacities, cataract is a leading cause of blindness worldwide. Because adverse sequelae of cataract surgery include CME and uveitis, cataract surgeons often prescribe prophylactic administration of both steroidal and non-steroidal anti-inflammatory eye drops. Non-steroidal anti-inflammatory agents are included in prophylaxis to avoid long-term, high dose exposure to corticosteroids, which can cause elevated intraocular pressure and glaucoma as noted above. This combination is also prescribed to expose both anterior and posterior tissues to prophylaxis. Current eye drops formulations of corticosteroidal anti-inflammatory agents, however, raise IOP at least temporarily and in some patients IOP can remain above normal.

In contrast to the IOP sequelae described above, the dexamethasone-loaded liquid depot provided herein has not resulted in clinically significant elevated IOP. This result is surprising considering that current steroidal eye drops that raise IOP include only 0.1% (wt) corticosteroid, while, in contrast, the embodiments described herein can include 10% to 15% (wt %) corticosteroid (for example, dexamethasone).

In one embodiment, the sustained-release liquid depot consists of about 10% dexamethasone, about 15% dexamethasone, or from 10% to 15% dexamethasone, such as about 10%, 11%, 12%, 13%, 14%, or about 15% (wt %), or any interval therebetween, in a balance of a liquid mixture comprising, consisting of, or consisting essentially of about 70% to about 80% tocopherol (such as about 70%, 71%, 72%, 73%, 74%, 75%, 76%, 77%, 78%, 79%, or about 80% (% wt), or an interval therebetween) and 20% to 30% film-forming excipient(s) (such as about 20%, 21%, 22%, 23%, 24%, 25%, 26%, 27%, 28%, 29%, or about 30% (% wt) or an interval therebetween). In a specific embodiment, the tocopherol is tocopheryl acetate and the film-forming excipient is MIGLYOL® 810.

In one embodiment, the sustained-release liquid depot consists of about 15% moxifloxacin, about 20% moxifloxacin, or from 15% to 20% moxifloxacin, such as about 15%, 16%, 17%, 18%, 19%, or about 20% (wt %), or any interval therebetween, in a balance of a liquid mixture comprising, consisting of, or consisting essentially of about 70% to about 80% tocopherol (such as about 70%, 71%, 72%, 73%, 74%, 75%, 76%, 77%, 78%, 79%, or about 80% (% wt), or an interval therebetween) and 20% to 30% film-forming excipient(s) (such as about 20%, 21%, 22%, 23%, 24%, 25%, 26%, 27%, 28%, 29%, or about 30% (% wt) or an interval therebetween). In a specific embodiment, the tocopherol is tocopheryl acetate and the film-forming excipient is an MCT or MIGLYOL® 810 N.

Further regarding film-forming excipients, Crodamol® GTCC or Crodamol® GTCC/C are fully saturated triesters, primarily caprylic/capric triglyceride, having a refractive index of 1.4485-1.4500 (n 20 D), low solubility in water, viscosity of 25-33 mPas (at 20° C.), and a relative density 0.93-0.96 g/cm³ (g/mL).

MIGLYOL® 818 is a triglyceride of the fractionated $C_8$ and $C_{10}$ plant fatty acids (caprylic/capric/linoleic triglyceride; contains about 4%-5% linoleic acid. Viscosity 30-35 mPa·s (20° C.); miscible in oils.

MIGLYOL® 829 (caprylic/capric/succinic triglyceride); caprylic/capric glyceride units crosslinked with succinic acid to form a larger molecule with unique properties; a glycerin ester of the fractionated $C_8$ and $C_{10}$ plant fatty acids, combined with succinic acid; viscosity is about 230 mPa·s (20° C.); high density of 1.00-1.02 g/cm³ M (20° C.); virtually non-miscible in water.

MIGLYOL® 840, CAS #77466-09-2 is a propylene glycol diester of saturated plant fatty acids with chain lengths of $C_8$ and $C_{10}$; majority caprylic acid, less capric acid, small amounts of caproic, lauric and myristic acids; density 0.91-0.93 g/cm³ (20° C.); viscosity 9-12 mPa s (20° C.); refractive index 1.440-1.442 n20D; miscible in oils.

Neobee® M5 is another fully saturated triester, primarily caprylic/capric triglyceride, having a refractive index of 1.4480-1.4510 (n 20 D), low solubility in water, viscosity of 25-33 mPas (20° C.), and relative density 0.94 g/cm³ at 20° C.

Not all excipients are suitable film-forming agents for use in the embodiments described herein. For example, although cholesterol (CAS #57-88-5) has a refractive index of 1.53 n 20 D, low solubility in water, and is used as a nonionic emulsifier, and although cholesterol has been included with cyclodextrins or Vaseline in preparations for treating dry eye, cholesterol was found unsuitable for use in a tocopherol-based liquid depot as described herein.

Further regarding tocopherols, α-Tocopherol: refractive index (RI) 1.503-1.507; practically insoluble in water; density 0.947-0.951 g/cm³; oil. Tocopherols are incompatible with peroxides and metal ions, especially iron, copper, and silver; d-Alpha tocopherol: CAS #59-02-9; oil; d-α-tocopherol is the naturally occurring form of alpha-tocopherol; d-Alpha tocopheryl acetate: CAS #58-95-7; oil; dl-Alpha tocopheryl acetate: CAS 7695-91-21; RI 1.4950-1.4972; density 0.953 g/cm3, unstable to alkali, more stable than alpha-tocopherol, oil; Beta tocopherol: oil; CAS #148-03-8; Delta tocopherol: CAS #119-13-1; oil; Gamma tocopherol: CAS #7616-22-01; α-Tocotrienol: Refractive index: 1.523; β-Tocotrienol: Refractive index: 1.52, oil.

In at least one embodiment, the liquid depot does not contain a pharmaceutical agent, (i.e., it comprises, consists of, or consists essentially of tocopherol and film forming excipient), and when instilled into the eye the liquid depot forms a film that provides a liquid "bandage." In one embodiment, the liquid bandage comprises, consists of, or consists essentially of tocopheryl acetate and triglycerides. In one embodiment, the liquid bandage comprises, consists of, or consists essentially of tocopheryl acetate and MIGLYOL® (neutral oil). In one embodiment, the liquid bandage has a viscosity of about 850 cP to about 1100 cP, inclusive. This embodiment may be useful, for example, in the re-epithelialization of larger corneal epithelial defects in patients who have undergone photorefractive keratectomy, or for more general prophylaxis or eye protection.

EXAMPLES

Example 1. Liquid Depot

Figure 3:
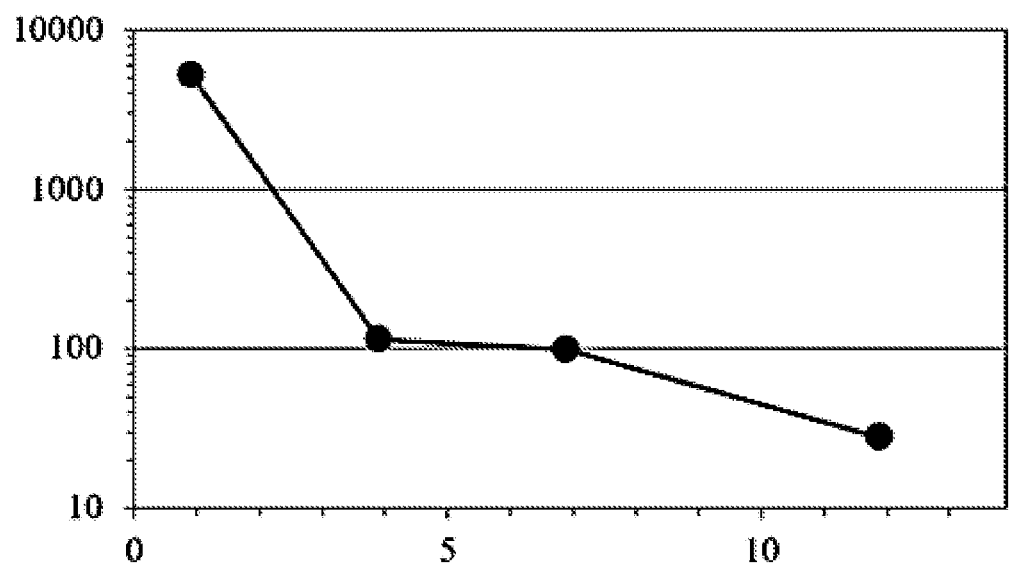
FIG. 3 shows the average amount of vitamin E acetate in tear samples collected from rabbit eyes on days 1, 4, 7, and 12 following administration of a single 50 μL depot of vitamin E acetate. During this same time course, vitamin E acetate was not observed in samples of aqueous humor. X-axis, days; y-axis, vitamin E acetate ng/mL.

To characterize a tocopherol-based liquid depot system, a single aliquot of 50 µL of vitamin E acetate was instilled into rabbit eyes. Subsequently, tear samples were collected using filter paper strips, and the vitamin E acetate contained in the paper strips extracted using methanol. The amount of vitamin E acetate in the methanol extracts was analyzed using LC/MS/MS by known methods. Vitamin E acetate was observed in tear samples collected on days 1, 4, 7, and 12, as shown in Table 1, and the results are shown graphically in FIG. 3.

TABLE 1

| Vitamin E acetate in rabbit tear sample from MeOH extract of paper strips | | |
|---|---|---|
| Day | Ave (ng/mL) | # of samples |
| 1 | 5249.50 | 4 |
| 4 | 114.13 | 4 |
| 7 | 98.63 | 4 |
| 12 | 27.40 | 6 |

Additionally, at days 1, 4, 7, and 12, aqueous humor samples were collected from four eyes using syringes, then analyzed for the amount of vitamin E acetate in each sample using LC/MS/MC (quantification limit 1.0 ng/mL). No detectable vitamin E acetate was observed in aqueous humor samples on days 1, 4, 7, or 12.

The results show that measurable amounts of vitamin E acetate was present in the tears of rabbit eyes for at least 12 days, showing the liquid depot was present in the eye for at least 12 days despite normal lacrimal and eye functions; but vitamin E acetate was not present in the anterior chamber of the eye, showing that the liquid depot was not absorbed into the eye.

Example 2. Comparison of Dexamethasone In Vitro Release

Figure 4:
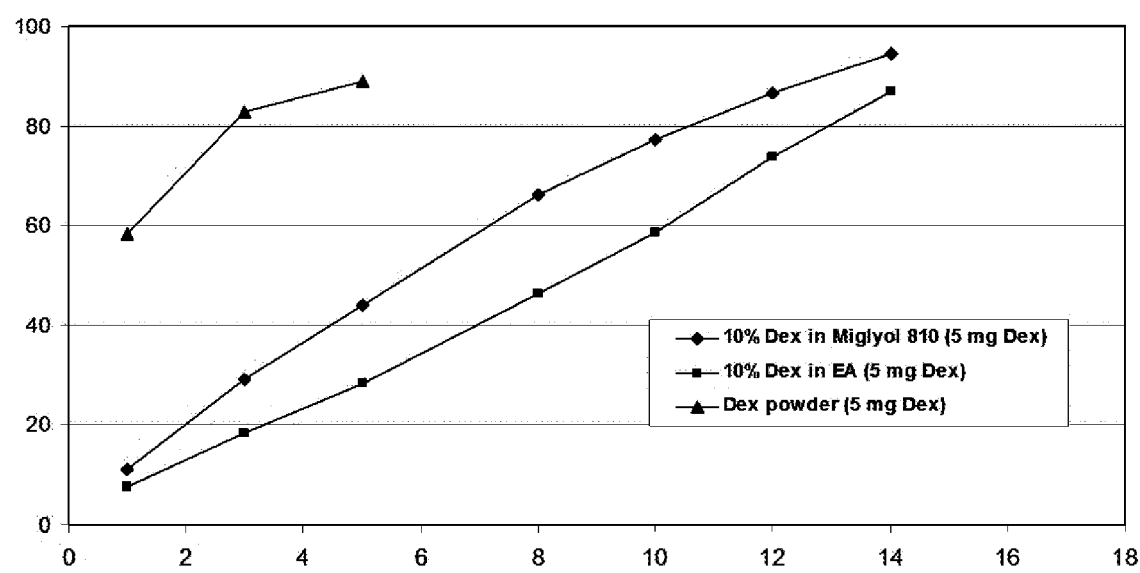
FIG. 4 is a graph showing in vitro release of 5 mg dexamethasone powder (▲), 5 mg dexamethasone in MIGLYOL® 810 (♦), or 5 mg dexamethasone in vitamin E acetate (■) in saline. Powder or 50 μL aliquots of liquid depot formulations were placed in 100 mL saline (50 mL exchange), and % dexamethasone release determined by UPLC. X-axis days; y-axis % total dexamethasone released into saline.

This Example compares in vitro release of dexamethasone power with two liquid formulations of dexamethasone (one using tocopherol, one using MIGLYOL®). The percent dexamethasone released from 5 mg dexamethasone powder, 10% dexamethasone (5 mg) in MIGLYOL® 810, or 10% dexamethasone (5 mg) in tocopherol acetate was tested in a 100 mL saline sink (50 mL exchange). The results are shown graphically in FIG. 4.

Example 3. Liquid Depot Comprising Dexamethasone

Vitamin E is viscous, having a cP (mPas) of approximate 6000-6500 (20° C.). In combination with a liquid film-forming excipient, in this Example MIGLYOL®, sustained release liquid depots comprising one or more of a number of pharmaceutical agents can be achieved. MIGLYOL® is the brand name for a suite of stable neutral oils that are designated generally recognized as safe (GRAS) by the United States Food and Drug Administration.

Figure 5:
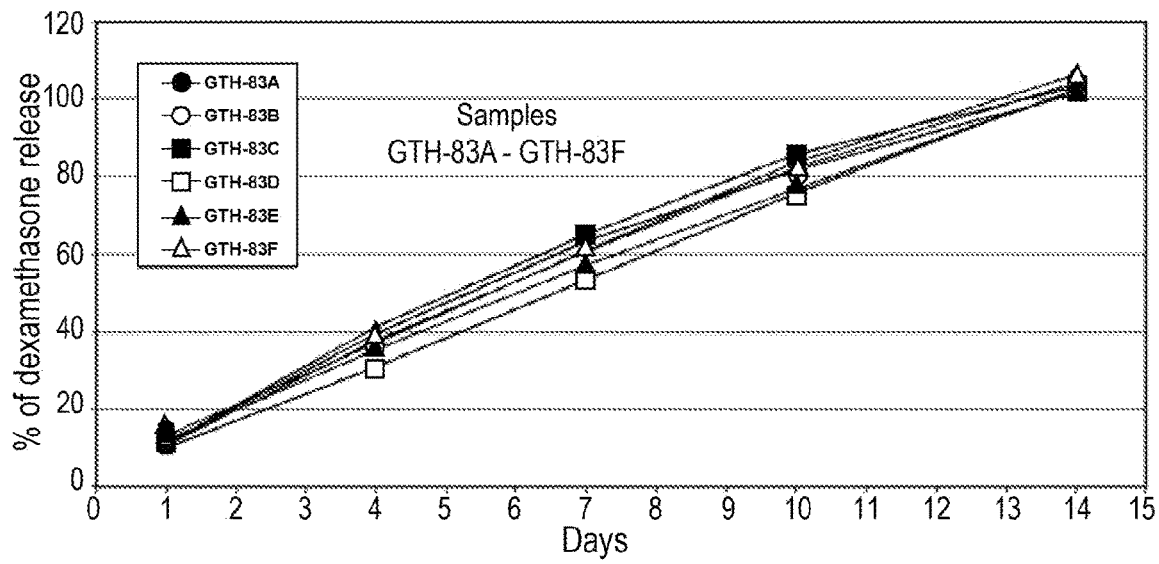
FIG. 5 is a graph showing in vitro release of dexamethasone from 50 μL aliquots of a liquid depot formulation (10% dexamethasone, 72% vitamin E acetate, and 18% MIGLYOL® 810 (medium chain triglycerides)), placed in 200 mL saline (100 mL exchange). Six replicates were tested: y-axis, % dexamethasone released; x-axis, days; ●: GTH-83A; ○: GTH-83B; ■: GTH-83C; □: GTH-83D; ▲: GTH-83E; Δ: GTH-83F.

A liquid depot was prepared by thoroughly mixing 10% dexamethasone, 72% vitamin E acetate, and 18% MIGLYOL® 810, (10% dexamethasone in 90% of a mixture of 80:20 tocopheryl acetate:MIGLYOL®). This dexamethasone-containing liquid depot had a viscosity of 850 cP-860 cP. A 50 µL aliquot was placed in 200 mL saline solution, then 100 mL withdrawn (and replaced with 100 mL fresh saline) at intervals, and the amount of dexamethasone determined by UPLC. The release profile of this formulation is shown in FIG. 5 (n=6, repetitions A-F); dexamethasone was released over ten days.

Another embodiment of a liquid depot was prepared by thoroughly mixing 10% dexamethasone, 72% vitamin E acetate, and 18% MIGLYOL® 810. The viscosity was measured in duplicate and indicated viscosity of 995 cP and 1008 cP (average 1001.5 cP); after three months, viscosity was measured at 1079 cP (average of all time points 1027 cP).

Example 4. In Vivo Release from Liquid Depot Comprising Dexamethasone

Figure 6:
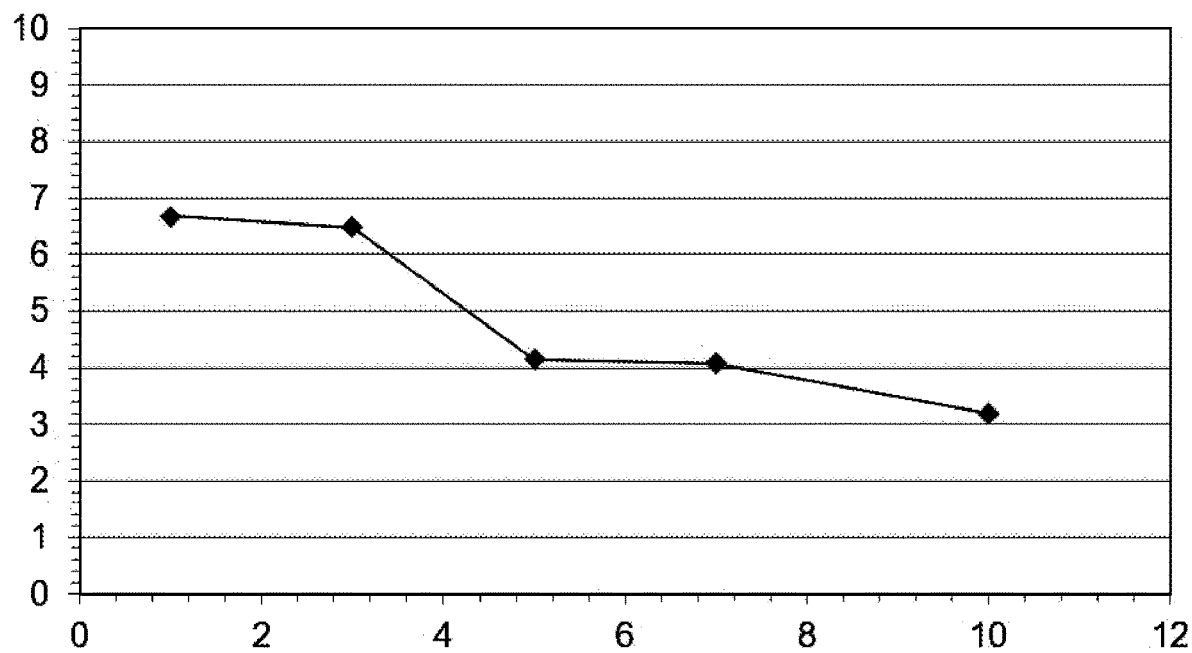
FIG. 6 is a graph showing the amount of dexamethasone detected in the anterior chamber of the eye in the days following instillation of a dexamethasone-containing liquid depot. X-axis, days; y-axis, dexamethasone ng/mL (average).

A formulation of dexamethasone:vitamin E acetate:MIGLYOL® 810 at a weight ratio of 10:72:18 was prepared. In a good laboratory practices (GLP) study, depots of 50 µL were instilled into each eye of New Zealand White (NZW) rabbits (either sex, 3.5-4 kilo), and the anterior chamber tapped subsequently and assayed by LCMS. The following Table 2 shows data and number of animals (N) per time point; and the results for dexamethasone detected in the anterior chamber are shown in FIG. 6.

TABLE 2

| Average dexamethasone level (ng/mL) in anterior chamber | | | | | |
|---|---|---|---|---|---|
| Day | 1 | 3 | 5 | 7 | 10 |
| Dexamethasone | 6.68 | 6.48 | 4.14 | 4.08 | 3.20 |
| N | 5 | 4 | 5 | 15 | 8 |

Example 5. Liquid Depot Delivery of Dexamethasone to the Interior of the Eye

A liquid depot was assembled by thoroughly mixing 80 mg tocopheryl acetate with 20 mg MIGLYOL® 810 (neutral oil). Ten (10) mg dexamethasone was suspended in 90 mg of the liquid depot, and the formulation mixed to a homogeneous liquid. The dexamethasone liquid depot was sterilized by radiation using standard protocols.

One 25 μL unit of the dexamethasone-liquid depot was instilled into the eyes of female New Zealand White rabbits. Subsequently, the amount of dexamethasone present in the eye tissues and fluids was determined at time points from 8 hours to 21 days. The data are shown in Table 3 and Table 4:

TABLE 3

Dexamethasone concentration (ng/mL, ng/g) in eye fluids and cornea

| | | | Aqueous Humor | | | Cornea | | | |
|---|---|---|---|---|---|---|---|---|---|
| Time | ID | Eye | Conc. (ng/mL) | Average (±SD) | Tissue (g) | Homog. (mL) | Homog. (ng/mL) | Tissue (ng/g) | Average (±SD) |
| Hr 8 | 1 | OD | 56.9 | 44.8 ± | 0.058 | 0.291 | 203 | 1015 | 560 ± |
|  |  | OS | 53.3 | 13.7 | 0.066 | 0.332 | 157 | 785 | 291 |
|  | 2 | OD | 48.5 |  | 0.051 | 0.256 | 107 | 535 |  |
|  |  | OS | 55.0 |  | 0.063 | 0.316 | 92.0 | 460 |  |
|  | 3 | OD | 25.1 |  | 0.056 | 0.282 | 49.2 | 246 |  |
|  |  | OS | 30.1 |  | 0.069 | 0.347 | 64.3 | 322 |  |
| Hr 24 | 4 | OD | 2.80 | 2.47 ± | 0.076 | 0.380 | 88.1 | 441 | 260 ± |
|  |  | OS | 5.00 | 1.35 | 0.083 | 0.417 | 28.4 | 142 | 132 |
|  | 5 | OD | 2.17 |  | 0.077 | 0.387 | 81.6 | 408 |  |
|  |  | OS | 1.94 |  | 0.059 | 0.294 | 46.0 | 230 |  |
|  | 6 | OD | 1.21 |  | 0.073 | 0.364 | 30.0 | 150 |  |
|  |  | OS | 1.69 |  | 0.071 | 0.354 | 37.4 | 187 |  |
| Day 3 | 7 | OD | BLOQ | 2.50 ± | 0.068 | 0.340 | 38.9 | 195 | 176 ± |
|  |  | OS | 0.507 | 2.54 | 0.063 | 0.313 | 13.5 | 67.5 | 111 |
|  | 8 | OD | 5.41 |  | 0.081 | 0.407 | 34.2 | 171 |  |
|  |  | OS | 0.667 |  | 0.069 | 0.345 | 9.89 | 49.5 |  |
|  | 9 | OD | 5.16 |  | 0.099 | 0.494 | 43.8 | 219 |  |
|  |  | OS | 0.779 |  | 0.067 | 0.334 | 70.6 | 353 |  |
| Day 8 | 10 | OD | BLOQ | 7.53 ± | 0.062 | 0.310 | 16.5 | 82.5 | 284 ± |
|  |  | OS | 13.8 | ND | 0.083 | 0.417 | 27.0 | 135 | 215 |
|  | 11 | OD | BLOQ |  | 0.057 | 0.287 | 46.7 | 234 |  |
|  |  | OS | 1.26 |  | 0.076 | 0.381 | 99.3 | 497 |  |
|  | 12 | OD | BLOQ |  | 0.057 | 0.283 | 121 | 605 |  |
|  |  | OS | BLOQ |  | 0.083 | 0.417 | 30.3 | 152 |  |
| Day 14 | 13 | OD | BLOQ | ND | 0.078 | 0.393 | 1.39 | 6.95 | 12.2 ± |
|  |  | OS | BLOQ |  | 0.076 | 0.378 | 0.837 | 4.19 | 6.33 |
|  | 14 | OD | BLOQ |  | 0.064 | 0.322 | 4.35 | 21.8 |  |
|  |  | OS | BLOQ |  | 0.109 | 0.544 | 2.20 | 11.0 |  |
|  | 15 | OD | 0.677 |  | 0.080 | 0.396 | 2.69 | 13.5 |  |
|  |  | OS | BLOQ |  | 0.073 | 0.365 | 3.19 | 16.0 |  |

TABLE 3

Dexamethasone concentration (ng/mL, ng/g) in eye fluids and cornea

| | | | Aqueous Humor | | | Cornea | | | |
|---|---|---|---|---|---|---|---|---|---|
| Time | ID | Eye | Conc. (ng/mL) | Average (±SD) | Tissue (g) | Homog. (mL) | Homog. (ng/mL) | Tissue (ng/g) | Average (±SD) |
| Day 21 | 16 | OD | BLOQ | ND | 0.066 | 0.328 | 0.698 | 3.49 | 8.14 ± |
|  |  | OS | BLOQ |  | 0.094 | 0.468 | 3.60 | 18.0 | 6.65 |
|  | 17 | OD | BLOQ |  | 0.056 | 0.279 | 1.09 | 5.45 |  |
|  |  | OS | BLOQ |  | 0.071 | 0.354 | 1.12 | 5.60 |  |

TABLE 4

Dexamethasone concentration (ng/mL, ng/g) in conjunctiva and iris/ciliary body

| Time | ID | Eye | Conjunctiva | | | | | Iris/Ciliary Body | | | | |
|---|---|---|---|---|---|---|---|---|---|---|---|---|
| | | | Tissue (g) | Homog. (mL) | Homog. (ng/mL) | Tissue (ng/g) | Average (±SD) | Tissue (g) | Homog. (mL) | Homog. (ng/mL) | Tissue (ng/g) | Average (±SD) |
| Hr 8 | 1 | OD | 0.085 | 0.426 | 317 | 1585 | 1659 ± 838 | 0.072 | 0.357 | 30.0 | 150 | 123 ± 33.9 |
| | | OS | 0.072 | 0.359 | 637 | 3185 | | 0.089 | 0.447 | 22.5 | 113 | |
| | 2 | OD | 0.099 | 0.494 | 295 | 1475 | | 0.065 | 0.326 | 31.4 | 157 | |
| | | OS | 0.068 | 0.342 | 308 | 1540 | | 0.067 | 0.337 | 30.2 | 151 | |
| | 3 | OD | 0.097 | 0.484 | 120 | 600 | | 0.081 | 0.405 | 16.6 | 83.0 | |
| | | OS | 0.116 | 0.578 | 314 | 1570 | | 0.069 | 0.345 | 17.2 | 86.0 | |
| Hr 24 | 4 | OD | 0.118 | 0.588 | 337 | 1685 | 598 ± 582 | 0.047 | 0.234 | 2.09 | 10.5 | 12.3 ± 4.87 |
| | | OS | 0.091 | 0.454 | 77.7 | 389 | | 0.101 | 0.504 | 2.18 | 10.9 | |
| | 5 | OD | 0.207 | 1.00 | 138 | 690 | | 0.067 | 0.337 | 4.17 | 20.9 | |
| | | OS | 0.123 | 0.614 | 29.5 | 148 | | 0.069 | 0.347 | 3.03 | 15.2 | |
| | 6 | OD | 0.148 | 0.742 | 117 | 585 | | 0.095 | 0.476 | 1.66 | 8.30 | |
| | | OS | 0.104 | 0.519 | 17.9 | 89.5 | | 0.091 | 0.457 | 1.66 | 8.30 | |
| Day 3 | 7 | OD | 0.160 | 0.801 | 19.7 | 98.5 | 372 ± 369 | 0.072 | 0.357 | 1.26 | 6.30 | 9.72 ± 13.31 |
| | | OS | 0.123 | 0.613 | 27.0 | 135 | | 0.086 | 0.432 | 0.594 | 2.97 | |
| | 8 | OD | 0.172 | 0.860 | 126 | 630 | | 0.182 | 0.910 | 0.753 | 3.77 | |
| | | OS | 0.153 | 0.765 | 11.4 | 57.0 | | 0.092 | 0.459 | 0.498 | 2.49 | |
| | 9 | OD | 0.137 | 0.684 | 198 | 990 | | 0.026 | 0.128 | 7.26 | 36.3 | |
| | | OS | 0.129 | 0.646 | 64.5 | 323 | | 0.070 | 0.348 | 1.30 | 6.50 | |
| Day 8 | 10 | OD | 0.092 | 0.459 | 128 | 640 | 1630 ± 1989 | 0.070 | 0.352 | 1.07 | 5.35 | 8.15 ± 6.80 |
| | | OS | 0.068 | 0.340 | 49.4 | 247 | | 0.079 | 0.396 | 0.533 | 2.67 | |
| | 11 | OD | 0.129 | 0.644 | 122 | 610 | | 0.067 | 0.334 | 0.651 | 3.26 | |
| | | OS | 0.125 | 0.623 | 402 | 2010 | | 0.065 | 0.325 | 2.85 | 14.3 | |
| | 12 | OD | 0.153 | 0.767 | 1100 | 5500 | | 0.082 | 0.408 | 3.80 | 19.0 | |
| | | OS | 0.065 | 0.326 | 155 | 775 | | 0.083 | 0.417 | 0.875 | 4.38 | |
| Day 14 | 13 | OD | 0.157 | 0.787 | 1.80 | 9.00 | 53.8 ± 63.2 | 0.075 | 0.376 | BLOQ | ND | 1.47 ± 0.459 |
| | | OS | 0.174 | 0.868 | 2.04 | 10.2 | | 0.079 | 0.396 | BLOQ | ND | |
| | 14 | OD | 0.089 | 0.445 | 4.02 | 20.1 | | 0.069 | 0.347 | 0.239 | 1.20 | |
| | | OS | 0.116 | 0.583 | 4.08 | 20.4 | | 0.086 | 0.429 | BLOQ | ND | |
| | 15 | OD | 0.152 | 0.759 | 32.2 | 161 | | 0.069 | 0.347 | 0.241 | 1.21 | |
| | | OS | 0.134 | 0.671 | 20.4 | 102 | | 0.091 | 0.456 | 0.399 | 2.00 | |
| Day 21 | 16 | OD | 0.096 | 0.482 | 8.48 | 42.4 | 28.2 ± 18.7 | 0.099 | 0.493 | BLOQ | ND | 3.88 ± ND |
| | | OS | 0.158 | 0.788 | 9.15 | 45.8 | | 0.069 | 0.346 | 1.33 | 6.65 | |
| | 17 | OD | 0.199 | 0.993 | 3.28 | 16.4 | | 0.086 | 0.431 | BLOQ | ND | |
| | | OS | 0.190 | 0.950 | 1.62 | 8.10 | | 0.076 | 0.378 | 0.222 | 1.11 | |

Limit of quantitation: 0.5 ng/mL for humors, 0.2 ng/mL for tissues; BLOQ: below limit of quantitation;
Homog: homogenate; OD: right eye; OS: left eye; SD: standard deviation; ND: not determined.

These data show that one instillation of the liquid depot resulted in dexamethasone in the conjunctiva, cornea, and iris/ciliary body (ICB) for at least 21 days; and in the aqueous humor for at least 8 days (more than a week). Importantly, this liquid depot was able to deliver dexamethasone to the interior liquid (humors) and tissues (iris/ciliary body) for at least a week (at least 7 days).

Example 6. Liquid Depot Comprising Prednisolone

Figure 7:
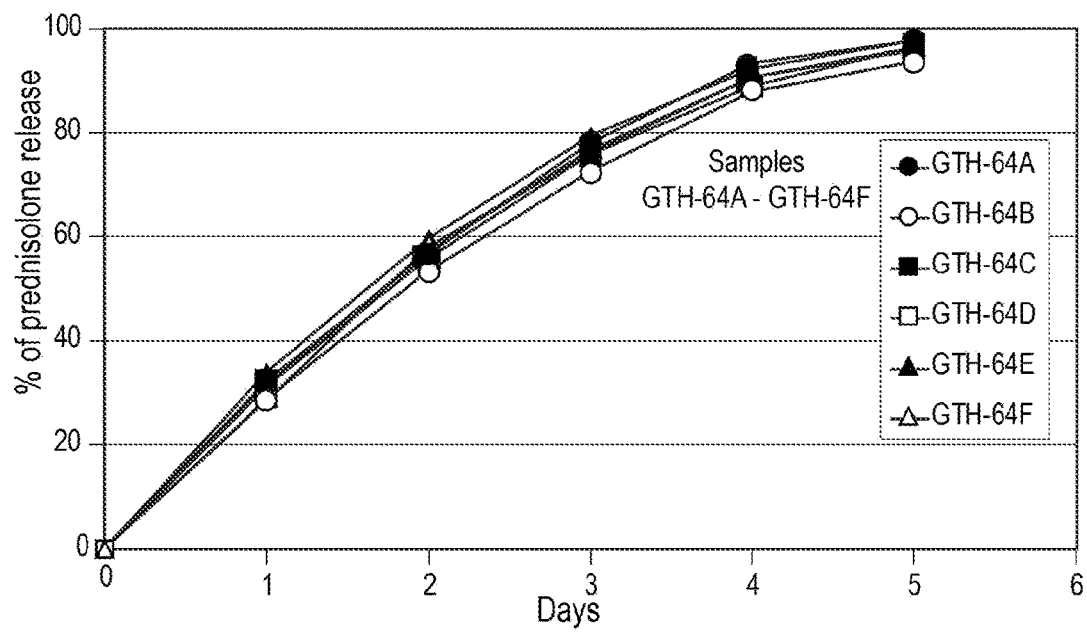
FIG. 7 is a graph showing in vitro release of prednisolone from a liquid depot formulation (10% prednisolone and 90% of a mixture of tocopheryl acetate:Miglyol® 810 (medium chain triglycerides) at a wt/wt ratio of about 80:20) placed in 100 gm water. For each time point, 60 ml sample was withdrawn for sampling and replaced with 60 mL saline. Six replicates were tested: y-axis, % prednisolone released; x-axis, days; ●: GTH-64A; ○: GTH-64B; ■: GTH-64C; □: GTH-64D; ▲: GTH-64E; Δ: GTH-64F.

A liquid depot was prepared by thoroughly mixing 10% prednisolone, 80% vitamin E acetate, and 20% MIGLYOL® 810, (10% prednisolone in 90% of a mixture of 80:20 tocopheryl acetate:MIGLYOL® 810). An in vitro sustained release study of prednisolone was carried out using Cabone rings (Wilton Brands LLC, Woodridge, IL 60517) with an outer dimension (OD) of 0.5 inch and an inner dimension (ID) of 0.281 inch. Samples, GTH-64A to GTH-64F, each weighing at 50.9 mg, 48.6 mg, 50.4 mg, 48.7 mg, 51.6 mg, and 49.3 mg, respectively (average weight=49.92; SD=1.24; RSD (relative standard deviation)=2.47) were each separately added into a 125 mL urine sample cup (with cap) containing 100 gm of water. A 0.5" Cabone ring was placed inside the cup. At each time point, 60 ml from each of the six samples was withdrawn for sampling and replaced with 60 ml saline. The amount of prednisolone released was determined by UPLC. The release profile of prednisolone-containing liquid depot formulation is shown in FIG. 7; prednisolone was released for at least 5 days.

TABLE 5

Prednisolone cumulative % released

| Time (Days) | GTH-64A | GTH-64B | GTH-64C | GTH-64D | GTH-64E | GTH-64F | Avg | SD | % RSD |
|---|---|---|---|---|---|---|---|---|---|
| 0 | 0 | 0 | 0 | 0 | 0 | 0 | | | |
| 1 | 32.3 | 28.7 | 31.4 | 33.9 | 31.1 | 28.5 | 31.0 | 2.1 | 6.8 |
| 2 | 56.9 | 53.5 | 57.3 | 59.9 | 56.1 | 58.1 | 57.0 | 2.1 | 3.7 |
| 3 | 78.2 | 72.7 | 76.8 | 79.6 | 75.9 | 76.2 | 76.6 | 2.3 | 3.0 |
| 4 | 93.5 | 88.1 | 90.8 | 92.4 | 89.2 | 90.6 | 90.7 | 2.0 | 2.2 |
| 5 | 97.9 | 93.8 | 95.9 | 97.8 | 96.3 | 96.4 | 96.4 | 1.5 | 1.6 |

Another prednisolone liquid depot was prepared by thoroughly mixing 10% prednisolone, 80% vitamin E acetate, and 20% Miglyol® 810, (10% prednisolone in 90% of a mixture of 80:20 tocopheryl acetate:Miglyol® 810). An in vitro sustained release study of prednisolone was carried out using a 12.7 mm Cabone ring (Wilton Brands LLC, Woodridge, Ill.). Six samples, 5A to 5F, each weighing at 48.2 mg, 48.5 mg, 48.1 mg, 49 mg, 51.7 mg, and 49.2 mg, respectively (average weight=49.1 mg; SD=1.34; % RSD=2.7) were incubated in 50 ml saline at 40° C. At each time point, 25 ml from each of the six samples was withdrawn for sampling and replaced with 25 ml saline. The amount of prednisolone released was determined by UPLC. The release profile of prednisolone-containing liquid depot formulation is shown in

TABLE 6

Figure 8:
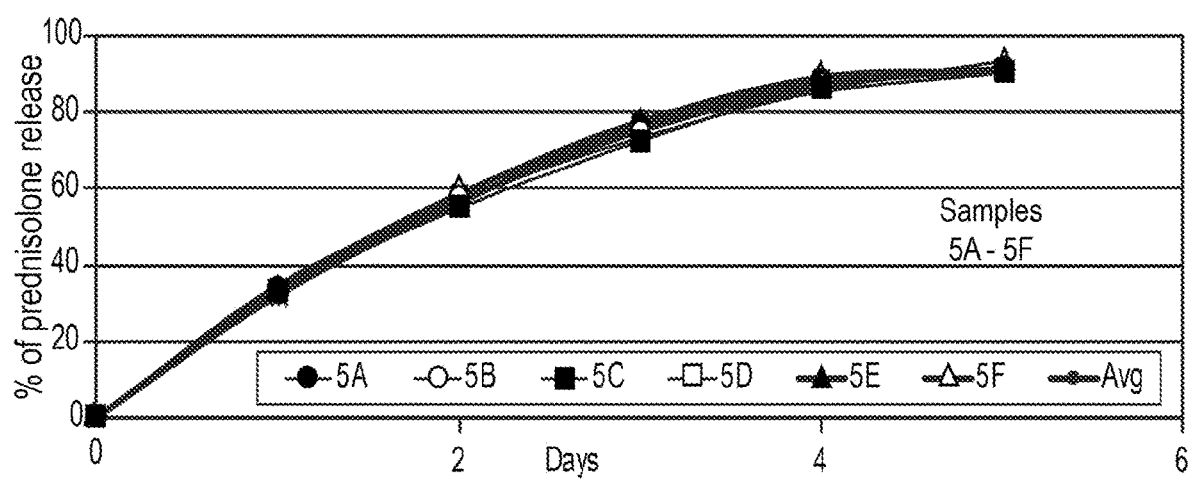
FIG. 8 is a graph showing in vitro release of prednisolone from a liquid depot formulation (10% prednisolone and 90% of a mixture of tocopheryl acetate:Miglyol® 810 (medium chain triglycerides) at a wt/wt ratio of about 80:20) that were placed in 100 gm water. For each time point, 50 ml sample was withdrawn for sampling and replaced with 50 mL saline. Six replicates were tested: y-axis, % prednisolone released; x-axis, days; ●: 5A; ○: 5B; ■: 5C; □: 5D; ▲: 5E; Δ: 5F; •: Avg.

Table 8 and FIG. 8; prednisolone was released for at least 5 days.

Prednisolone cumulative % released

| Time (Days) | 5A | 5B | 5C | 5D | 5E | 5F | Avg | SD | % RSD |
|---|---|---|---|---|---|---|---|---|---|
| 0 | 0 | 0 | 0 | 0 | 0 | 0 | 0 | | |
| 1 | 34.8 | 32.5 | 32.6 | 33.9 | 31.9 | 33.5 | 33.2 | 1.1 | 3.2 |
| 2 | 56.9 | 56.6 | 54.8 | 57.2 | 56.0 | 58.5 | 56.7 | 1.3 | 2.2 |
| 3 | 76.5 | 75.4 | 72.5 | 73.4 | 77.0 | 77.7 | 75.4 | 2.1 | 2.8 |
| 4 | 88.0 | 85.1 | 86.8 | 85.9 | 88.9 | 88.4 | 87.2 | 1.5 | 1.7 |
| 5 | 92.0 | 90.0 | 91.9 | 93.6 | 90.6 | 91.6 | 91.6 | 1.2 | 1.4 |

TABLE 7

Amount of prednisolone released (µg)

| Time (Days) | 5A | 5B | 5C | 5D | 5E | 5F | Avg | SD | % RSD |
|---|---|---|---|---|---|---|---|---|---|
| 1 | 1678.5 | 1576.0 | 1568.0 | 1659.0 | 1650.0 | 1650.0 | 1630.3 | 46.4 | 2.8 |
| 2 | 1065.3 | 1167.0 | 1065.5 | 1145.0 | 1246.5 | 1229.5 | 1153.1 | 77.7 | 6.7 |
| 3 | 942.8 | 915.0 | 852.8 | 792.8 | 1086.3 | 944.8 | 922.4 | 99.5 | 10.8 |
| 4 | 556.0 | 471.3 | 689.3 | 611.5 | 612.0 | 525.0 | 577.5 | 76.6 | 13.3 |
| 5 | 64.1 | 79.3 | 82.3 | 126.3 | 29.3 | 52.3 | 72.3 | 32.8 | 45.4 |

TABLE 8

Average concentration of prednisolone released

| Time (Days) | Avg (µg/mL) | SD | % RSD |
|---|---|---|---|
| 1 | 32.6 | 0.9 | 2.8 |
| 2 | 39.4 | 1.7 | 4.3 |
| 3 | 38.1 | 2.6 | 6.8 |
| 4 | 30.6 | 1.7 | 5.6 |
| 5 | 19.6 | 1.7 | 8.6 |

TABLE 9

Average concentration of loteprednol released

| Sample ID | Day | µg/mL | µg/100 mL | Total Release | Release/ day (µg) | Total release (%) |
|---|---|---|---|---|---|---|
| 66-A1 | 1 | 10.89 | 1089.0 | 1089.0 | 1089.0 | 15.2 |
| 66-A2 | 3 | 13.33 | 788.5 | 1877.5 | 394.3 | 26.1 |
| 66-A3 | 7 | 18.30 | 1163.5 | 3041.0 | 290.9 | 42.4 |
| 66-A4 | 10 | 15.80 | 665.0 | 3706.0 | 221.7 | 51.6 |
| 66-A5 | 14 | 15.85 | 795.0 | 4501.0 | 198.8 | 62.7 |
| 66-B1 | 1 | 8.12 | 812.0 | 812.0 | 812.0 | 13.6 |
| 66-B2 | 3 | 13.90 | 984.0 | 1796.0 | 492.0 | 30.0 |
| 66-B3 | 7 | 17.94 | 1099.0 | 2895.0 | 274.8 | 48.4 |
| 66-B4 | 10 | 10.45 | 148.0 | 3043.0 | 49.3 | 50.9 |
| 66-B5 | 14 | 14.93 | 970.5 | 4013.5 | 242.6 | 67.1 |

TABLE 10

Loteprednol cumulative % released

| Time (Days) | 66-A | 66-B | Avg | SD | % RSD |
|---|---|---|---|---|---|
| 1 | 15.2 | 13.6 | 14.4 | 1.1 | 7.8 |
| 3 | 26.1 | 30.0 | 28.1 | 2.7 | 9.8 |
| 7 | 42.4 | 48.4 | 45.4 | 4.3 | 9.4 |
| 10 | 51.6 | 50.9 | 51.3 | 0.5 | 1.0 |
| 14 | 62.7 | 67.1 | 64.9 | 3.1 | 4.8 |

Example 7. Liquid Depot Comprising Loteprednol

Figure 9:
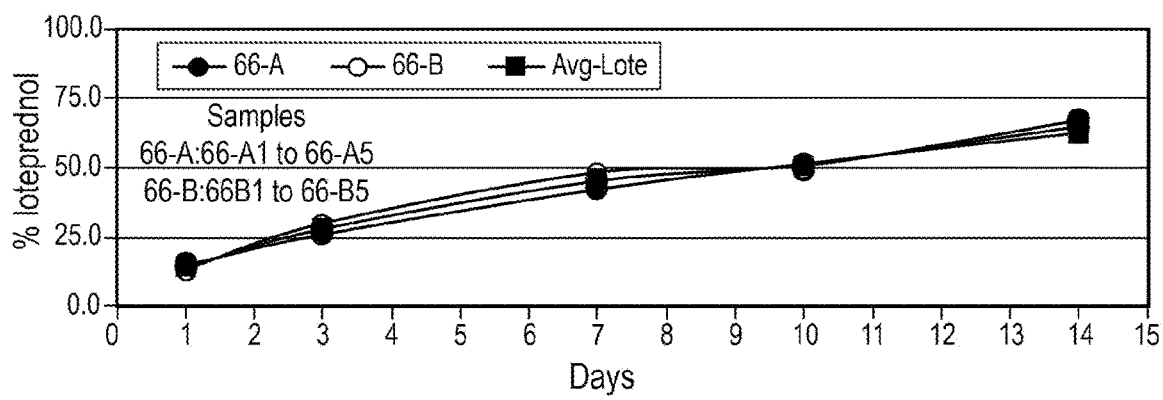
FIG. 9 is a graph showing in vitro release of loteprednol from a loteprednol-containing liquid depot formulation (10% loteprednol and 90% of a mixture of tocopheryl acetate:Miglyol® 810 (medium chain triglycerides) at a wt/wt ratio of about 80:20). Fifty mL of each sample were withdrawn for sampling and replaced with 50 mL of 40% methanol/water. Two replicates were tested: y-axis, % loteprednol released; x-axis, days; ●: 66-A; ○: 66-B; •: Avg.

A liquid depot was prepared by thoroughly mixing 10% loteprednol, 80% vitamin E acetate, and 20% MIGLYOL® 810, (10% loteprednol in 90% of a mixture of 80:20 tocopheryl acetate:MIGLYOL® 810). The in vitro sustained release study of loteprednol was carried out by incubating two samples, 66-A and 66-B, each weighing at about 71.8 mg and 59.8 mg, respectively in 100 mL of 40% methanol/water at 37° C. At each time point, 50 ml from each of the two samples was withdrawn for sampling and replaced with 50 mL of 40% methanol/water. The amount of loteprednol released was determined by UPLC. The release profile of loteprednol-containing liquid depot formulation is shown in Table 9, Table 10, and FIG. 9; loteprednol was released for at least 14 days.

Example 8. Liquid Depots Comprising Prednisone, Triamcinolone, or Fluorometholone Prednisone is loaded into a depot of tocopherol and MIGLYOL® as in Example 3. In vitro and in vivo sustained release data are collected as in Examples 3-5.

Triamcinolone is loaded into a depot of tocopherol and MIGLYOL® as in Example 3. In vitro and in vivo sustained release data are collected as in Examples 3-5.

Fluorometholone is loaded into a depot of tocopherol and MIGLYOL® as in Example 3. In vitro and in vivo sustained release data are collected as in Examples 3-5.

Example 9. Liquid Depot Comprising Moxifloxacin

Figure 10:
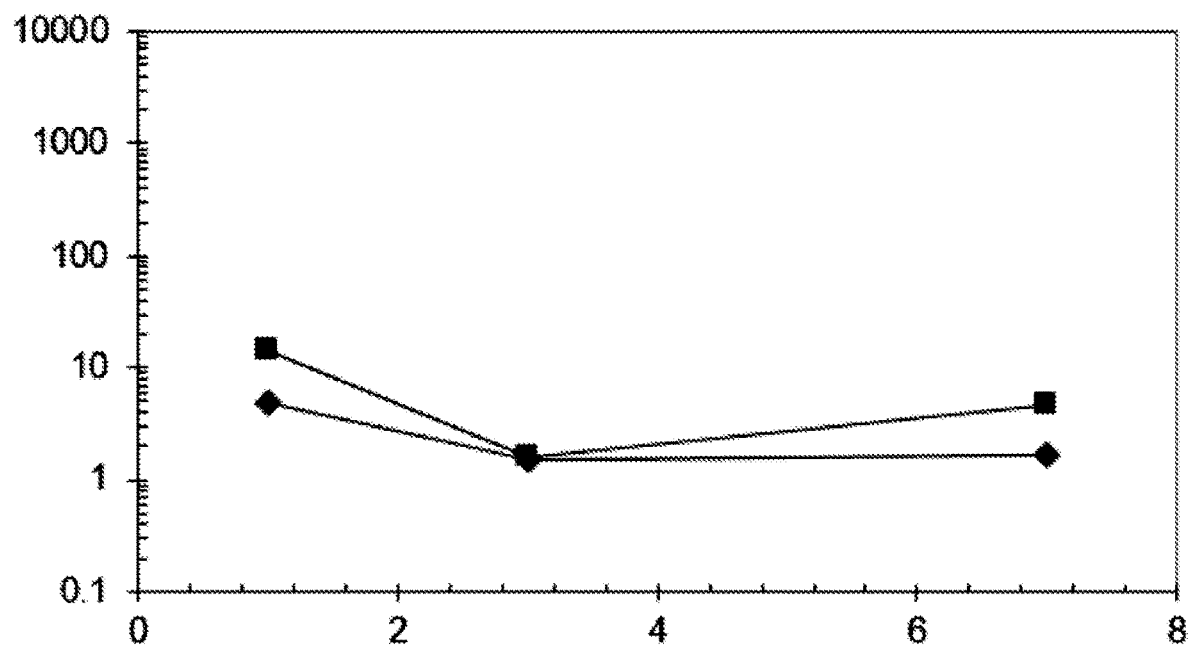
FIG. 10 is a graph showing the amount of moxifloxacin in rabbit tears days after a single instillation of either 15% (♦) or 20% (■) moxifloxacin-containing liquid depots. X-axis, days; y-axis, moxifloxacin μg/mL (average, n=6).
Figure 11:
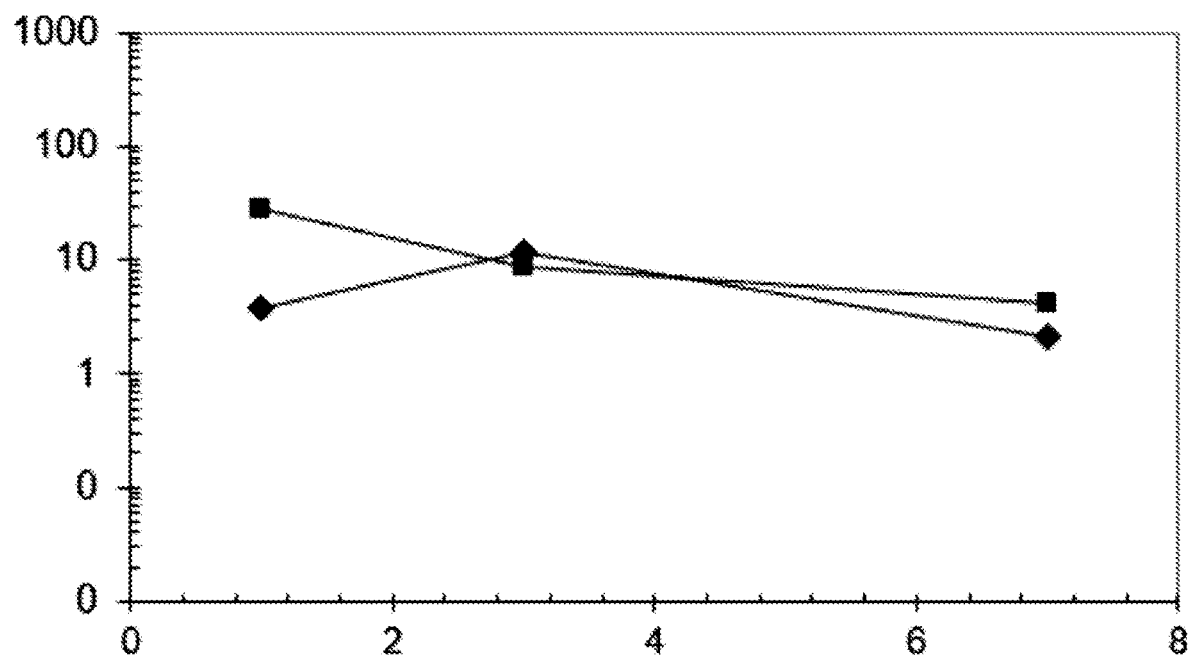
FIG. 11 is a graph showing the amount of moxifloxacin detected in the anterior chamber of the eye in the days following a single instillation of either 15% (♦) or 20% (■) moxifloxacin-containing liquid depots. X-axis, days; y-axis, moxifloxacin ng/mL (average, n=6).

Moxifloxacin was loaded into a depot of tocopherol and MIGLYOL® as in Example 3, and in vivo sustained release data were collected as in Examples 3-5. More specifically, two liquid depots were prepared: one containing 15% (wt %) moxifloxacin (the balance 70:30 EA:MIGLYOL® 810 N), one containing 20% (wt %) moxifloxacin (the balance 70:30 EA:MIGLYOL® 810 N). One drop of liquid depot was instilled into each eye of several test rabbits, and tears collected on days 1, 3, and 7. Moxifloxacin was identified and quantified in tear samples by LC/MS/MS. FIG. 10 evidences the amount of moxifloxacin in rabbit tears on days 1, 3, and 7 after a single instillation of either 15% (♦) or 20% (■) moxifloxacin-containing liquid depots. Moxifloxacin was detected in tear samples 7 days after a single application, showing that the liquid depots provided therapeutic dosing on the surface of the eye for at least 7 days. Aqueous humor was also tapped on days 1, 3, and 7. FIG. 11 evidences the amount of moxifloxacin in the anterior chamber on days 1, 3, and 7 after a single instillation of either 15% (♦) or 20% (■) moxifloxacin-containing liquid depots. Moxifloxacin was detected in aqueous humor samples 7 days after a single application, showing that both liquid depots provided therapeutic dosing in the anterior chamber of the eye for at least 7 days.

Example 10. Liquid Depots Comprising Ciprofloxacin

Figure 12:
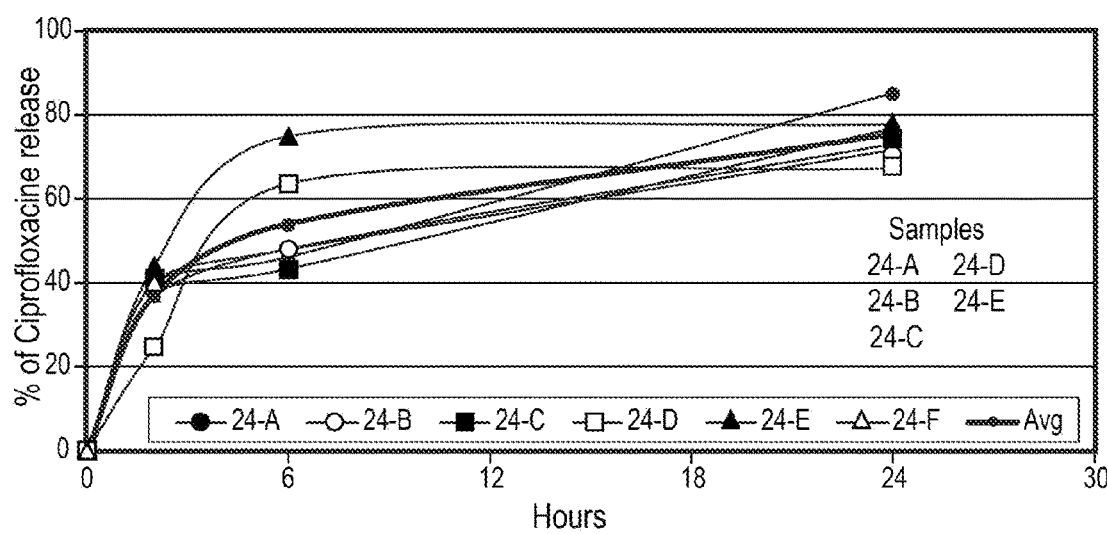
FIG. 12 is a graph showing in vitro release of ciprofloxacin from a ciprofloxacin-containing liquid depot formulation (15% ciprofloxacin and 85% of a mixture of tocopheryl acetate:Miglyol® 810 (medium chain triglycerides) at a wt/wt ratio of about 70:30). Twenty-five mL of each sample were withdrawn for sampling and replaced with 25 mL of saline. Six replicates were tested: y-axis, % ciprofloxacin released; x-axis, hours; ●: 24-A; ○: 24-B; ■: 24-C; □: 24-D; ▲: 24-E; Δ: 24-F; •: Avg.

A liquid depot was prepared by thoroughly mixing 15% ciprofloxacin hydrochloride, 70% vitamin E acetate, and 30% MIGLYOL® 810, (15% ciprofloxacin in 85% of a mixture of 70:30 tocopheryl acetate:MIGLYOL® 810). The in vitro sustained release study of ciprofloxacin was carried out using a Cabone ring of 12.7 mm. Six samples, Cipro-24A to Cipro-24F, each weighing at 50.2 mg, 54.1 mg, 56.3 mg, 44 mg, 62.3 mg and 61 mg, respectively (average weight=54.65 mg; SD=6.857; % RSD=12.5) were incubated in 50 mL saline at 40° C. At each time point, 25 ml from each of the six samples was withdrawn for sampling and replaced with 25 mL saline. The amount of ciprofloxacin released was determined by UPLC. The release profile of ciprofloxacin-containing liquid depot formulation is shown in Table 11, Table 12, and FIG. 12; ciprofloxacin was released for at least 24 hours.

TABLE 11

Ciprofloxacin cumulative % released

| Time (Hours) | 24-A | 24-B | 24-C | 24-D | 24-E | 24-F | Avg | SD | % RSD |
|---|---|---|---|---|---|---|---|---|---|
| 0 | 0 | 0 | 0 | 0 | 0 | 0 | 0 | | |
| 2 | 36.5 | 40.1 | 37.4 | 24.4 | 44.1 | 40.0 | 37.1 | 6.7 | 18.2 |
| 6 | 48.1 | 47.9 | 43.3 | 63.5 | 75.0 | 46.2 | 54.0 | 12.5 | 23.1 |
| 24 | 73.0 | 71.5 | 76.7 | 67.2 | 77.8 | 85.2 | 75.2 | 6.2 | 8.2 |

TABLE 12

Average concentration of ciprofloxacin released

| Time (Hours) | Avg (ug/mL) | SD | % RSD |
|---|---|---|---|
| 2 | 61.8 | 17.2 | 27.9 |
| 6 | 57.7 | 22.3 | 38.6 |
| 24 | 64.5 | 19.6 | 30.3 |

Example 11. Liquid Depot Comprising Ciprofloxacin

Figure 13:
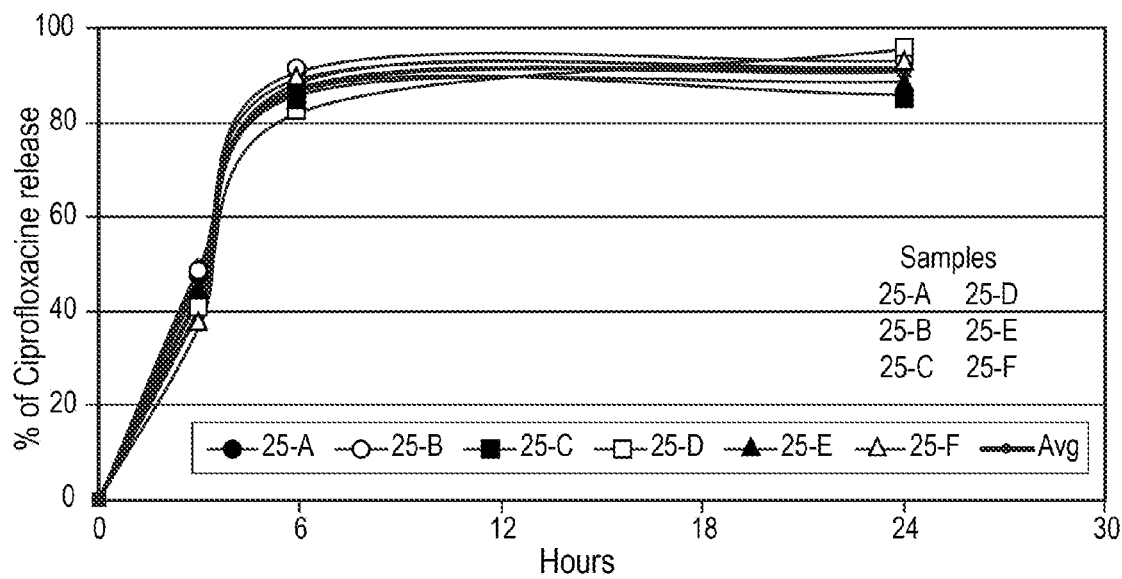
FIG. 13 is a graph showing another in vitro release of ciprofloxacin from a ciprofloxacin-containing liquid depot formulation (15% ciprofloxacin and 85% of a mixture of tocopheryl acetate:Miglyol® 810 (medium chain triglycerides) at a wt/wt ratio of about 70:30). Twenty-five mL of each sample were withdrawn for sampling and replaced with 25 mL of saline. Six replicates were tested: y-axis, % ciprofloxacin released; x-axis, hours; ●: 25-A; ○: 25-B; ■: 25-C; □: 25-D; ▲: 25-E; Δ: 25-F; •: Avg.

Another liquid depot comprising ciprofloxacin similar to Example 8 was prepared by thoroughly mixing 15% ciprofloxacin hydrochloride, 70% vitamin E acetate, and 30% MIGLYOL® 810, (15% ciprofloxacin in 85% of a mixture of 70:30 tocopheryl acetate:MIGLYOL® 810). The in vitro sustained release study of ciprofloxacin was carried out using a 12.7 mm Cabone ring. Six samples, Cipro-25A to Cipro-25F, each weighing at 45.8 mg, 48.5 mg, 51.2 mg, 48 mg, 62.2 mg, and 49.3 mg, respectively (average weight=50.83 mg; SD=5.839; % RSD=11.5) were incubated in 50 mL saline at 40° C. At each time point, 25 ml from each of the six samples was withdrawn for sampling and replaced with 25 mL saline. The amount of ciprofloxacin released was determined by UPLC. The release profile of ciprofloxacin-containing liquid depot formulation is shown in Table 13, Table 14, and FIG. 13; ciprofloxacin was released for at least 24 hours.

TABLE 13

Ciprofloxacin cumulative % released

| Time (Hours) | 25-A | 25-B | 25-C | 25-D | 25-E | 25-F | Avg | SD | % RSD |
|---|---|---|---|---|---|---|---|---|---|
| 0 | 0 | 0 | 0 | 0 | 0 | 0 | 0 | | |
| 3 | 49.6 | 48.0 | 40.5 | 40.9 | 45.9 | 37.0 | 43.7 | 4.9 | 11.3 |
| 6 | 89.3 | 90.8 | 86.7 | 82.2 | 85.7 | 88.7 | 87.2 | 3.1 | 3.5 |
| 24 | 91.8 | 93.0 | 86.0 | 95.5 | 88.4 | 91.4 | 91.0 | 3.4 | 3.7 |

TABLE 14

Average concentration of ciprofloxacin released

| Time (Hours) | Avg (ug/mL) | SD | % RSD |
|---|---|---|---|
| 3 | 66.6 | 10.9 | 16.4 |
| 6 | 99.6 | 10.7 | 10.7 |
| 24 | 55.5 | 6.9 | 12.4 |

Example 12. Liquid Depots Comprising Gatifloxacin

Figure 14:
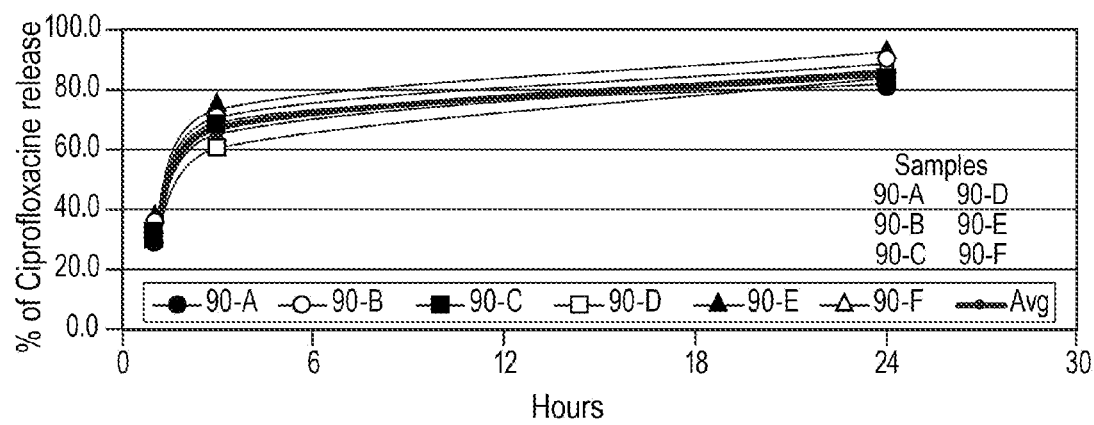
FIG. 14 is a graph showing in vitro release of gatifloxacin from a gatifloxacin-containing liquid depot formulation (10% gatifloxacin and 90% of a mixture of tocopheryl acetate:Miglyol® 810 (medium chain triglycerides) at a wt/wt ratio of about 70:30). Twenty mL of each sample were withdrawn for sampling and replaced with 20 mL of saline. Six replicates were tested: y-axis, % gatifloxacin released; x-axis, hours; ●: 90-A; ○: 90-B; ■: 90-C; □: 90-D; ▲: 90-E; Δ: 90-F; •: Avg.

A liquid depot was prepared by thoroughly mixing 10% gatifloxacin, 70% vitamin E acetate, and 30% MIGLYOL® 810, (10% gatifloxacin in 90% of a mixture of 70:30 tocopheryl acetate:MIGLYOL® 810). The in vitro sustained release study of gatifloxacin was carried out using a Cabone ring (Wilton Brands LLC, Woodridge, Ill. 60517) of 12.7 mm. Six samples, Gati-90A to Gati-90F, each weighing at 48.2 mg, 48 mg, 48.9 mg, 47 mg, 49.1 mg, and 47.8 mg, respectively (average weight=48.17 mg; SD=0.766; % RSD=1.6) were incubated in 40 mL saline at 40° C. [At each time point, 20 ml from each of the six samples was withdrawn for sampling and replaced with 20 mL saline. The amount of gatifloxacin released was determined by UPLC. The release profile of gatifloxacin-containing liquid depot formulation is shown in Table 15, Table 16, and FIG. 14; gatifloxacin was released for at least 24 hours.

TABLE 15

Gatifloxacin cumulative % released

| Time (Hours) | 90-A | 90-B | 90-C | 90-D | 90-E | 90-F | Avg | SD | % RSD |
|---|---|---|---|---|---|---|---|---|---|
| 1 | 30.7 | 33.7 | 32.5 | 29.7 | 35.8 | 31.2 | 32.3 | 2.2 | 6.9 |
| 3 | 68.8 | 70.8 | 67.2 | 60.4 | 73.1 | 65.1 | 67.5 | 4.5 | 6.6 |
| 24 | 81.7 | 88.9 | 84.4 | 84.0 | 92.3 | 85.9 | 86.2 | 3.8 | 4.4 |

TABLE 16

Average concentration of gatifloxacin released

| Time (Hours) | Avg μg/mL | SD | % RSD |
|---|---|---|---|
| 1 | 38.9 | 3.2 | 8.2 |
| 3 | 61.9 | 5.0 | 8.1 |
| 24 | 53.4 | 3.2 | 6.0 |

Example 13. Liquid Depots Comprising Anti-Infectives (e.g., Levofloxacin, Gentamicin, Tobramycin or Chloramphenicol)

Levofloxacin is loaded into a depot of tocopherol and MIGLYOL® as in Example 3. In vitro and in vivo sustained release data are collected as in Examples 3-5.

Gentamicin is loaded into a depot of tocopherol and MIGLYOL® as in Example 3. In vitro and in vivo sustained release data are collected as in Examples 3-5.

Tobramycin is loaded into a depot of tocopherol and MIGLYOL® as in Example 3. In vitro and in vivo sustained release data are collected as in Examples 3-5.

Chloramphenicol is loaded into a depot of tocopherol and MIGLYOL® as in Example 3. In vitro and in vivo sustained release data are collected as in Examples 3-5.

Example 14. Liquid Depots Comprising Anti-Allergy Agents

Ketotifen is loaded into a depot of tocopherol and MIGLYOL® as in Example 3. In vitro and in vivo sustained release data are collected as in Examples 3-5.

Lodoxamine is loaded into a depot of tocopherol and MIGLYOL® as in Example 3. In vitro and in vivo sustained release data are collected as in Examples 3-5.

Azelastine is loaded into a depot of tocopherol and MIGLYOL® as in Example 3. In vitro and in vivo sustained release data are collected as in Examples 3-5.

Olopatadine is loaded into a depot of tocopherol and MIGLYOL® as in Example 3. In vitro and in vivo sustained release data are collected as in Examples 3-5.

Epinastine is loaded into a depot of tocopherol and MIGLYOL® as in Example 3. In vitro and in vivo sustained release data are collected as in Examples 3-5.

Example 15. Liquid Depot Comprising Latanoprost

Figure 15:
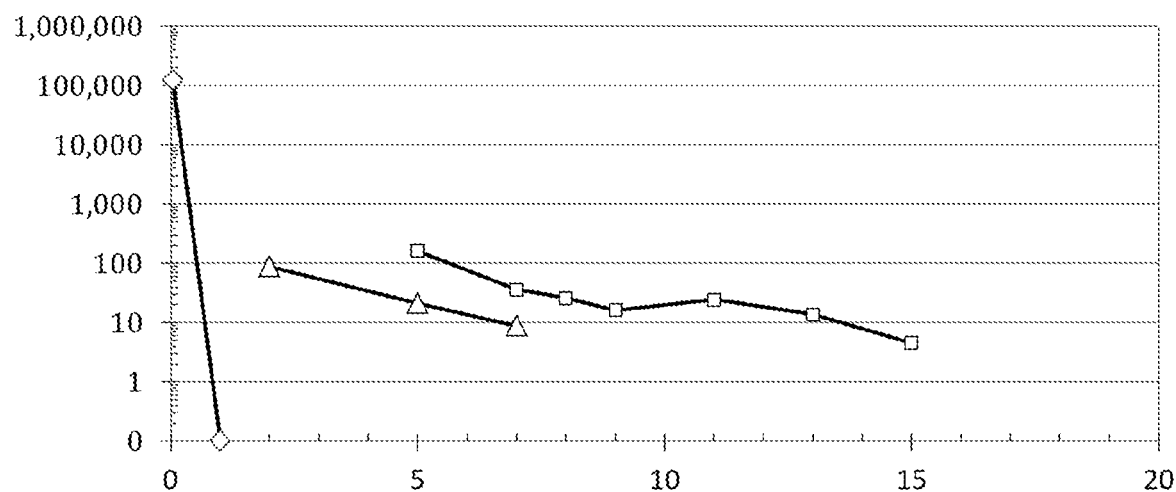
FIG. 15 is a graph showing the levels of latanoprost acid in the anterior chamber following a single drop of commercially available product (Xalatan® (latanoprost ophthalmic solution) 0.005%) or a one-time 50 µL instillation of one of two liquid depot latanoprost formulations. Each time point represents average of four samples taken from the anterior chamber of NZW rabbits (4.0-4.5 kg). y-axis: latanoprost acid pg/mL; x-axis: days following instillation; ◇: One drop Xalatan® (latanoprost ophthalmic solution) 0.005%; □: a 50 µL instillation of 0.05% latanoprost in 80:20 EA:Miglyol®812; Δ: a 50 µL instillation of 0.03% latanoprost in 80:20 EA:Miglyol®812.

Latanoprost was loaded into a liquid depot of 80:20 tocopheryl acetate:Miglyol® 812 at two different concentrations as described herein to provide sustained release formulation A (0.05% latanoprost in 80:20 EA:Miglyol®812) and formulation B (0.03% latanoprost in 80:20 EA:Miglyol®812). A commercial formulation, Xalatan® (latanoprost ophthalmic solution) 0.005%, was used as a comparator. Xalatan® (latanoprost ophthalmic solution) 0.005% is supplied as a sterile, isotonic, buffered aqueous solution of latanoprost with a pH of approximately 6.7 and an osmolality of approximately 267 mOsmol/kg. One drop of Xalatan® vs 50 µL of formulation A or B was instilled once in the eyes of 4.0-4.5 kg NZW rabbits. Samples from the anterior chamber were collected, four eyes per time point, and the concentration of latanoprost acid determined as described herein. As shown in FIG. 15, a one-time 50 µL instillation of formulation B (0.03% latanoprost) provided detectable latanoprost acid in the anterior chamber for at least 7 days; a one-time 50 µL instillation of formulation A (0.05% latanoprost) provided detectable latanoprost acid in the anterior chamber for at least 15 days.

Example 16. Liquid Depot Comprising a NSAID

Figure 16:
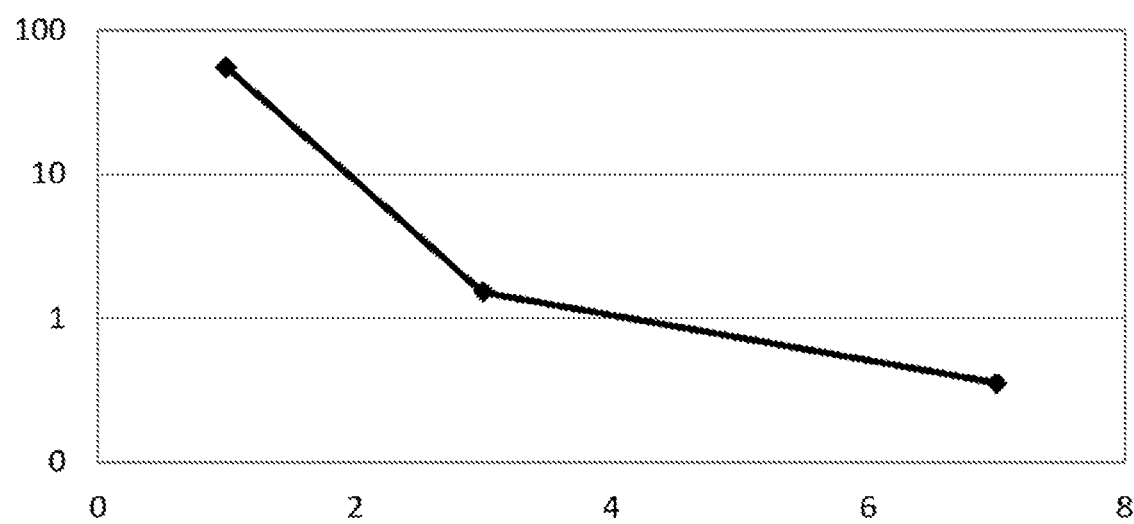
FIG. 16 is a graph showing results of an in vivo PK study of diclofenac acid drug level in tear samples following instillation of a liquid depot comprising 10% diclofenac acid in a 90% excipient mixture of 80:20 tocopheryl acetate:Miglyol®. y-axis: ng diclofenac/mg tear; x-axis: day.

A formulation of the NSAID diclofenac was prepared by thoroughly mixing 10% diclofenac acid in a 90% liquid depot mixture of 80:20 tocopheryl acetate:Miglyol®. A one-time application of 50 µL of this formulation was instilled into the eyes of NZW rabbits, and then tear samples were collected and analyzed as described herein. The results, as shown in FIG. 16, indicate that diclofenac was detected in the rabbit tear film for a least 7 days.

Example 17. Liquid Depot Comprising Cyclosporin

Figure 17:
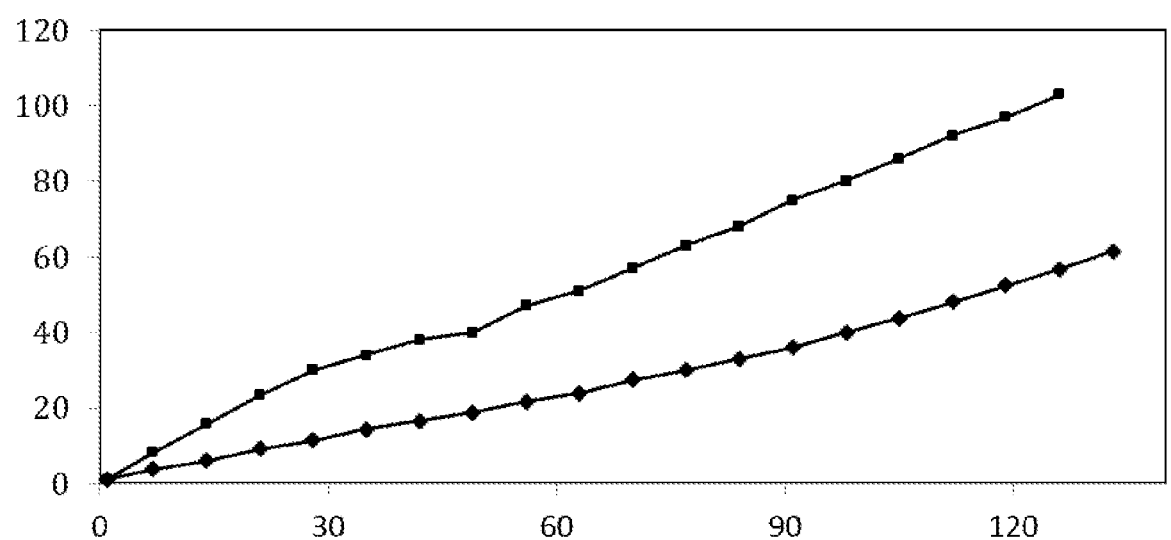
FIG. 17 is a graph showing in vitro release of cyclosporin from two liquid depots containing 2% cyclosporine in an excipient mixture of either 90:10 tocopheryl acetate:Miglyol®812 (♦) or 70:30 tocopheryl acetate:Miglyol®812 (■). y-axis: cyclosporin A total release (%); x-axis: days.

Two formulations comprising 2% cyclosporin A (CsA) were prepared as provided herein. One formulation contained 2% CsA in a mixture of 90:10 tocopheryl acetate:Miglyol®812; the other contained 2% CsA in a mixture of 70:30 tocopheryl acetate:Miglyol®812. The in vitro release (% CsA release) was monitored as described herein, and the total % release of CsA plotted over the course of at least 120 days, as shown in FIG. 17.

Example 18. Liquid Depot Applications

A sustained-release liquid depot loaded with a therapeutic agent is administered as a single application or provided in form of a kit to a subject who wears contact lens or make up. Because of the physical consistency, no running of the liquid depot is observed in the subject's eyes. In addition, the subject does not experience blurring of vision or eye irritation. Accordingly, at least one embodiment provides a kit comprising at least one single-use dispenser, wherein the at least one single-use dispenser comprises the liquid depot as described herein.

What is claimed is:

1. A method of treating glaucoma in a subject in need thereof, comprising topically administering to an eye of the subject with an eyedropper, a liquid depot consisting of latanoprost from 0.03% to 0.05%; tocopheryl acetate from 80% to 85% (wt %) and medium-chain triglycerides from 15%-20% (wt %); and wherein the liquid depot has a viscosity of no more than 1100 cP.

2. The method of claim 1, wherein the latanoprost is 0.05%.

3. The method of claim 1, wherein the medium-chain triglycerides are decanoyl/octanoyl glycerides.

4. The method of claim 1, wherein treatment reduces intraocular pressure in the eye.

5. The method of claim 1, wherein the tocopheryl acetate is at about 80% (wt %) and medium-chain triglycerides is at about 20% (wt %).

6. The method of claim 1, wherein the liquid depot consists of 0.03% latanoprost, 80% (wt %) tocopheryl acetate and 20% (wt %) medium-chain triglycerides, wherein the medium-chain triglycerides are decanoyl/octanoyl glycerides.

7. The method of claim 1, wherein the liquid depot consists of 0.05% latanoprost, 80% (wt %) tocopheryl acetate and 20% (wt %) medium-chain triglycerides, wherein the medium-chain triglycerides are decanoyl/octanoyl glycerides.

* * * * *